(12) United States Patent
Matula, Jr. et al.

(10) Patent No.: US 10,363,386 B2
(45) Date of Patent: Jul. 30, 2019

(54) PATIENT INTERFACE DEVICE

(71) Applicant: RIC INVESTMENTS LLC, Wilmington, DE (US)

(72) Inventors: Jerome Matula, Jr., Monroeville, PA (US); Jason P. Eaton, Hunker, PA (US); Steven C. Stegman, Gibsonia, PA (US); Luke Stonis, Columbus, OH (US); Greg Merz, Grahanna, OH (US); Keith Aaron Grider, Columbus, OH (US); Nic Davirro, Chicago, IL (US); Christopher D. Von Dohlen, Columbus, OH (US); Justin Rothermel, Pittsburgh, PA (US)

(73) Assignee: RIC INVESTMENTS LLC, Wilmington, DE (US)

( * ) Notice: Subject to any disclaimer, the term of this patent is extended or adjusted under 35 U.S.C. 154(b) by 414 days.

(21) Appl. No.: 14/076,526

(22) Filed: Nov. 11, 2013

(65) Prior Publication Data
US 2014/0060544 A1 Mar. 6, 2014

Related U.S. Application Data

(63) Continuation of application No. 13/022,736, filed on Feb. 8, 2011, now Pat. No. 8,596,271, which is a (Continued)

(51) Int. Cl.
*A61M 16/06* (2006.01)
*A61M 16/08* (2006.01)

(52) U.S. Cl.
CPC ........ *A61M 16/06* (2013.01); *A61M 16/0611* (2014.02); *A61M 16/0683* (2013.01);
(Continued)

(58) Field of Classification Search
CPC .............. A61M 16/06; A61M 16/0818; A61M 16/0683; A61M 16/0605; A61M 16/0622;
(Continued)

(56) References Cited

U.S. PATENT DOCUMENTS 4,367,735 A 1/1983 Dali
4,422,456 A * 12/1983 Tiep .................. A61M 16/0666
128/207.17
(Continued)

FOREIGN PATENT DOCUMENTS

WO WO2004073778 A1 9/2004
WO WO2012085758 A1 6/2012

OTHER PUBLICATIONS

Resmed, "Mirage Swift tm Nasal Pillows System from ResMed", 2004, ResMed Ltd.

*Primary Examiner* — Gregory A Anderson
*Assistant Examiner* — Margaret M Luarca
(74) *Attorney, Agent, or Firm* — Michael W. Haas

(57) ABSTRACT

A patient interface device that includes a support member sized and configured to span at least a portion of a patient's face while remaining below the patient's eyes responsive to the patient interface device being donned by such a patient and a sealing assembly operatively coupled to the support member such that the support member is moveable relative to the support member. The support member defines a gas carrying conduit adapted to carry a flow of gas to the sealing assembly. The support member is a single-piece unitary member and includes a conduit coupling portion adapted to be coupled to a patient circuit.

9 Claims, 32 Drawing Sheets

Related U.S. Application Data continuation of application No. 12/118,905, filed on May 12, 2008, now Pat. No. 7,900,628, which is a continuation of application No. 11/374,942, filed on Mar. 14, 2006, now Pat. No. 7,370,652, which is a continuation-in-part of application No. 11/074,410, filed on Mar. 8, 2005, now Pat. No. 7,856,982.

(60) Provisional application No. 60/552,136, filed on Mar. 11, 2004.

(52) U.S. Cl.
CPC ..... *A61M 16/0816* (2013.01); *A61M 16/0616* (2014.02); *A61M 16/0825* (2014.02); *A61M 16/0833* (2014.02); *A61M 2209/088* (2013.01); *A61M 2210/0618* (2013.01)

(58) Field of Classification Search
CPC .... A61M 2209/088; A61M 2210/0618; A61M 16/0672; A61M 16/0666
See application file for complete search history.

(56) References Cited

U.S. PATENT DOCUMENTS

| | | | |
|---|---|---|---|
| 4,782,832 A * | 11/1988 | Trimble | A61M 16/0666 128/204.18 |
| 4,915,105 A * | 4/1990 | Lee | A62B 18/00 128/205.27 |
| 4,949,128 A | 4/1990 | Kopala | |
| 5,724,865 A | 3/1998 | Handke | |
| 5,724,965 A | 3/1998 | Handke | |
| 6,019,101 A | 2/2000 | Cotner | |
| 6,119,694 A * | 9/2000 | Correa | A61M 16/0666 128/207.13 |
| 6,374,826 B1 | 4/2002 | Gunaratnam | |
| 6,478,026 B1 | 11/2002 | Wood | |
| 6,595,215 B2 | 7/2003 | Wood | |
| 6,769,432 B1 | 8/2004 | Keifer | |
| 6,889,689 B1 | 5/2005 | Neuman | |
| 7,201,169 B2 | 4/2007 | Wilkie | |
| 7,219,669 B1 | 5/2007 | Lovell | |
| 7,318,437 B2 | 1/2008 | Gunaratnam | |
| 2002/0096176 A1 | 7/2002 | Gunaratnam | |
| 2002/0122746 A1 * | 9/2002 | Yamamori | G01N 1/22 422/83 |
| 2003/0034030 A1 | 2/2003 | Carlucci | |
| 2003/0145857 A1 | 8/2003 | Sullivan | |
| 2003/0154987 A1 | 8/2003 | Palmer | |
| 2003/0172936 A1 | 9/2003 | Wilkie | |
| 2003/0183227 A1 | 10/2003 | Klemperer | |
| 2004/0025885 A1 | 2/2004 | Payne | |
| 2004/0226566 A1 | 11/2004 | Gunaratnam | |
| 2004/0261797 A1 | 12/2004 | White | |
| 2005/0011524 A1 * | 1/2005 | Thomlinson | A61M 16/0666 128/207.18 |
| 2005/0028822 A1 | 2/2005 | Sleeper | |
| 2006/0137690 A1 | 6/2006 | Gunaratnam | |

* cited by examiner

PATIENT INTERFACE DEVICE

CROSS-REFERENCE TO RELATED APPLICATIONS

This application is a Continuation of and claims priority under 35 U.S.C. § 120 from U.S. patent application Ser. No. 13/022,736, filed Feb. 8, 20118 which is a Continuation of and claims priority under 35 U.S.C. § 120 from U.S. patent application Ser. No. 12/118,905, filed May 12, 2008, now U.S. Pat. No. 7,900,628, which is a Continuation of and claims priority under 35 U.S.C. § 120 from U.S. patent application Ser. No. 11/374,942, filed Mar. 14, 2006, now U.S. Pat. No. 7,370,652, which is a Continuation-In-Part (CIP) and claims priority under 35 U.S.C. § 120 from U.S. patent application Ser. No. 11/074,410, filed Mar. 8, 2005, now U.S. Pat. No. 7,856,982, which claims priority under 35 U.S.C. § 119(e) from provisional U.S. patent application Ser. No. 60/552,136, filed Mar. 11, 2004, the contents of which each of which are incorporated herein by reference.

BACKGROUND OF THE INVENTION

1. Field of the Invention

The present invention pertains to a patient interface device that provides a stable platform supporting a sealing assembly for coupling a flow of gas with an airway of a patient, is relatively small to minimize the amount of material supported on the patient's face and head, and yet provides a high degree of adjustability, so that the patient interface device fits comfortably on a wide variety of differently sized and shaped patients.

2. Description of the Related Art

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provides a tight enough seal against a patient's face without discomfort. A problem arises in that in order for the mask to maintain a seal without any undue gas leaks around the periphery of the mask, the mask cushion may be compressed against the patient's face. This is most notable, for example, in masks having a bubble type cushion. While the bubble cushion itself is comfortable, it does not provide adequate support, which may cause gas leaks around the periphery of the mask. The bubble effect is diminished when the headgear strap force is increased to improve stability.

Some conventional respiratory masks attempt to enhance mask stability by providing a relatively large structure that must be mounted on the patient's face. Therefore, an advantage exists for a respiratory mask that minimizes the amount of material that must be supported on the patient's head and face, yet provides a relatively high degree of stability, so that that the mask is not easily dislodged from the patient. Another advantage exists for a respiratory mask that evenly distributes the headgear strapping force needed to hold the mask on the patient at locations on the patient's face that are best suited to handle such forces.

A further advantage exists for a respiratory mask that avoids providing any structural features near the patient's eyes. This advantage is particularly important for patient's who desire to wear glasses while wearing the mask and for patient's that tend to feel claustrophobic when a structure is provided at or near their eyes. Avoiding the ocular area also eliminates or avoids the leakage of gas into the user's eyes, which can cause great discomfort. A still further advantage exists for a mask that accomplishes these functions while also providing a relatively high degree of adjustability, so that a common mask style or configuration can be fitted to a variety of differently sized and shaped patients.

SUMMARY OF THE INVENTION

Accordingly, it is an object of the present invention to provide a patient interface device that overcomes the shortcomings of conventional interface devices. This object is achieved according to one embodiment of the present invention by providing a patient interface device that includes a support member sized and configured to span at least a portion of a patient's face while remaining below the patient's eyes responsive to the patient interface device being donned by such a patient and a sealing assembly operatively coupled to the support member such that the support member is moveable relative to the support member. The support member defines a gas carrying conduit adapted to carry a flow of gas to the sealing assembly. The support member is a single-piece unitary member and includes a conduit coupling portion adapted to be coupled to a patient circuit.

These configurations for the patient interface device of the present invention provide a stable platform that supports the sealing assembly on the patient, while minimizing the amount of material worn on the patient's face and head. It also provides a high degree of adjustability, so that the patient interface device fits comfortably on a wide variety of differently sized and shaped patients.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
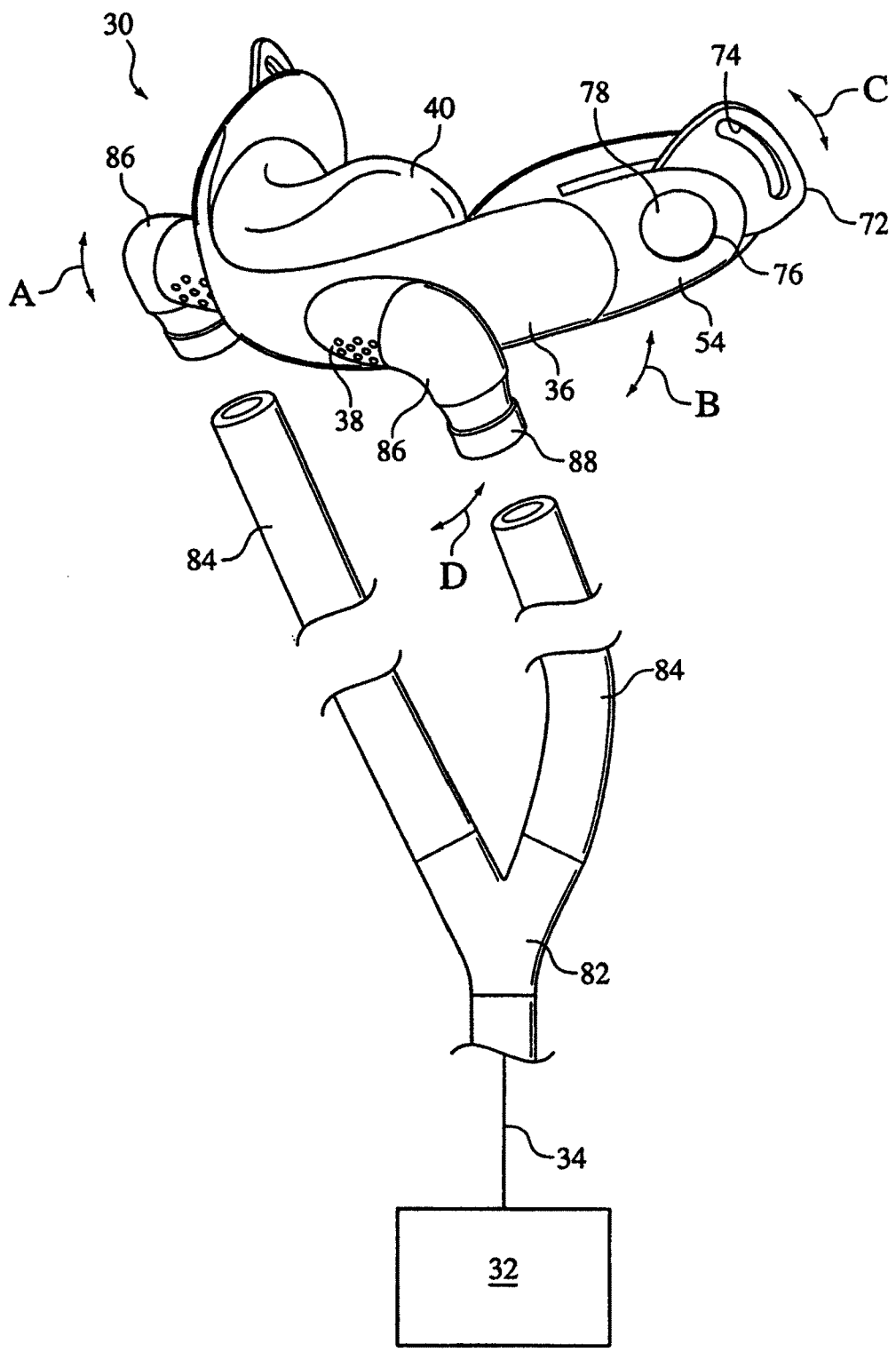
FIG. 1 is a perspective view of a first embodiment of a patient interface device according to the principles of the present invention shown schematically connected to a pressure support system.

FIGS. 1-4 illustrate a first embodiment of a patient interface device 30 according to the principles of the present invention. Patient interface device 30 is shown schematically connected to a pressure support system 32 via a patient circuit 34, which communicates gas from the pressure support system to the patient interface device. Pressure support system 32 is any conventional ventilation or pressure support system.

Examples of such pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device.

Patient interface device 30 includes a frame 36 sized and configured to span at least a portion of a patient's face while remaining below the patient's eyes when the patient interface device is donned by the patient. FIG. 2 shows patient interface device 30 being worn by a patient. A support member 38 is adjustably coupled to frame 36. In an exemplary embodiment, support member 38 is tubular shaped and inserts through a pair of slots provided in the frame and rotates relative to the frame, as indicated by arrow A in FIG. 1. The frame and support member are preferably formed from a rigid, lightweight material, such as plastic. However, frame 36 is preferably slightly bendable to allow it to flex when the patient interface device is donned by the patient.

A sealing assembly 40 is attached to support member 38. In the embodiment shown in FIGS. 1-4, sealing assembly 40 is a cushion type of seal that includes a sealing surface 42 adapted to engage a surface of a patient and to surround a patient's nares. An opening 44 is provided in seal 40 to communicate an interior of the seal with an airway of the patient. It can thus be appreciated that sealing assembly 40, in this embodiment, functions much like a conventional nasal seal. Sealing assembly 40 is preferably formed from a unitary piece of material, such as silicone, rubber, foam, or gel. It is to be understood, however, that other materials, in addition to or in place of these materials, can be used in the sealing assembly. The present invention also contemplates that the sealing assembly can be formed from a combination of materials, such as rigid, semi-rigid, and non-rigid materials to provide support for the cushion where desired. The sealing assembly can also include features associated with conventional sealing seals or cushions, such as providing one or more flaps at a distal end portion of the seal, providing an adhesive on at least a portion of the patient contacting surface of the seal, or any combination thereof.

Figure 3:
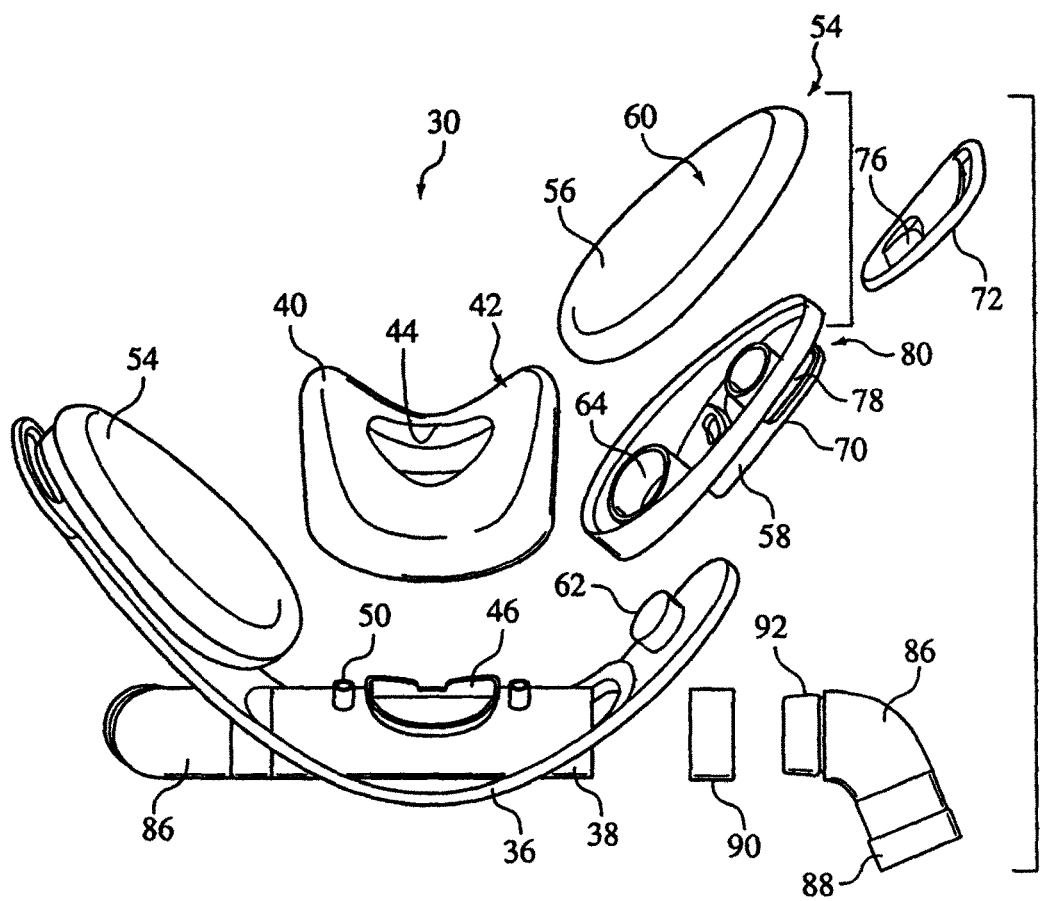
FIG. 3 is an exploded view of the patient interface device of FIG. 1.
Figure 4:
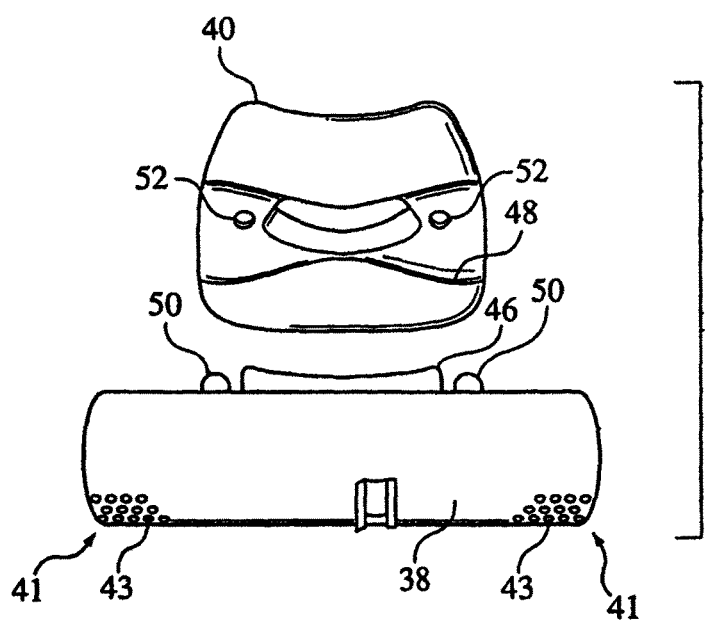
FIG. 4 is an exploded view showing the connection of the sealing assembly to the support member in the patient interface device of FIG. 1.
Figure 5:
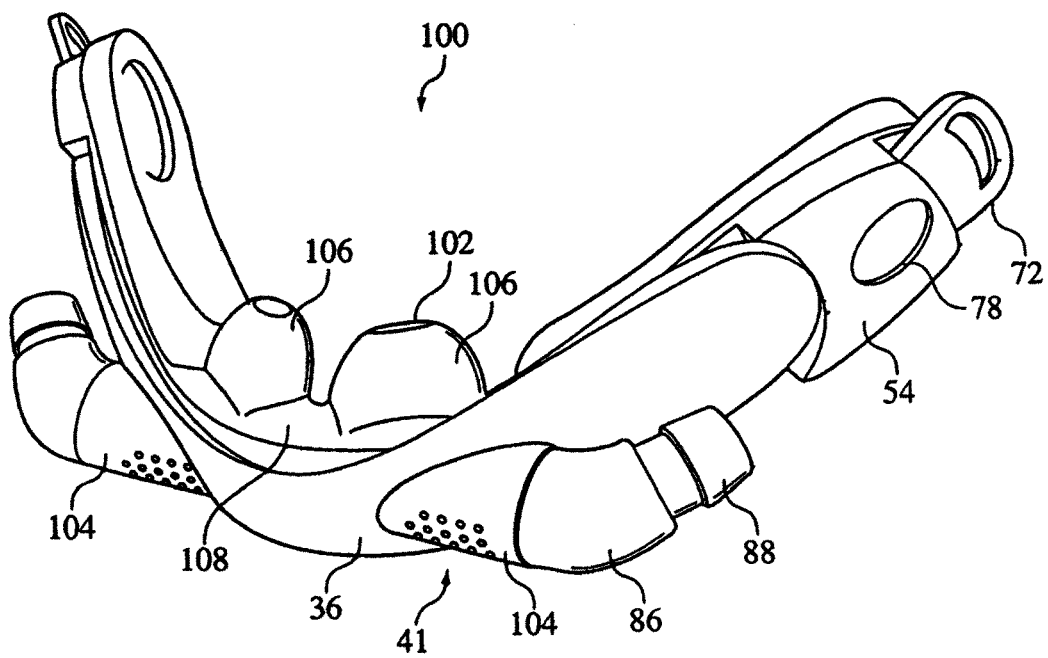
FIG. 5 is a perspective view of a second embodiment of a patient interface device according to the principles of the present invention.
Figure 6:
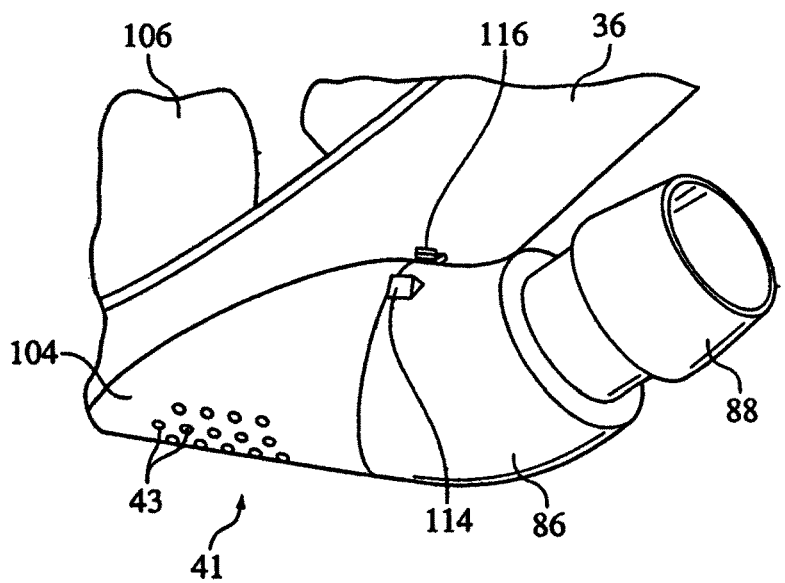
FIG. 6 is a detailed view of the support member and the frame in the patient interface device of FIG. 5.
Figure 7:
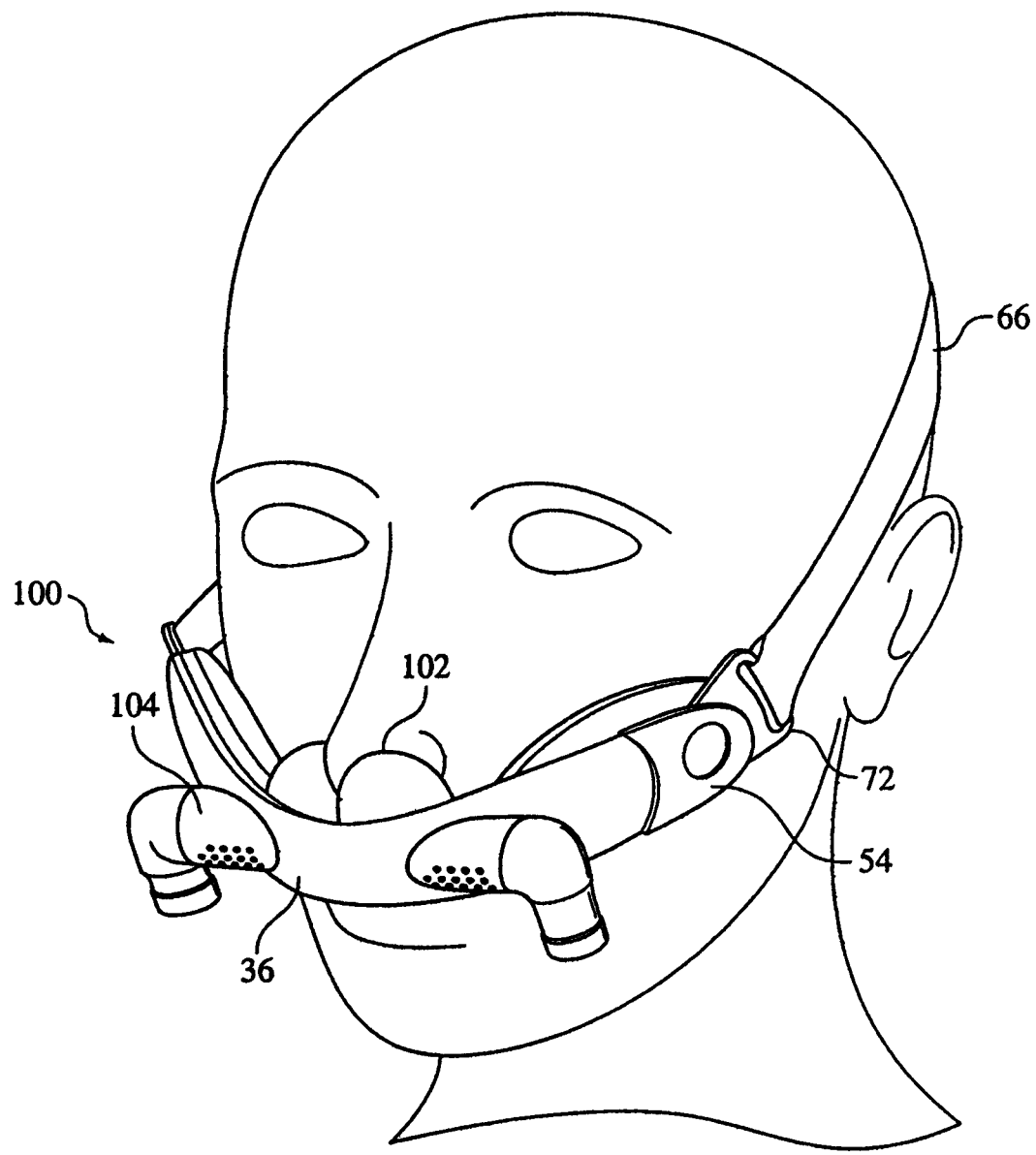
FIG. 7 is a perspective view of the patient interface device of FIG. 5 shown being worn by a patient.

As best shown in FIGS. 3 and 4, sealing assembly 40 attaches to support member 38 by mounting the sealing assembly on a support flange 46 provided on the support member. Support flange 46 includes an opening to communicate gas from an interior of the support member to the interior of the seal. A channel 48 is also provided on the support member contacting surface of sealing assembly 40 so that the sealing assembly slips at least partially around the circumference of the support member. To further assist in attaching and aligning the sealing assembly on the support member, a pair of tabs 50 are provided on the support member. Tabs 50 insert into respective detents 52 provided in sealing assembly 40. An alternative configuration for attaching the sealing assembly to the support member in a snap-on configuration is illustrated in FIGS. 46-49 and discussed below.

Because the patient interface device of the present invention is intended for use in a non-invasive ventilation-type of ventilation/pressure support system, an exhaust assembly 41 must be provided along the gas flow path to allow the patient's exhaled gasses to vent to atmosphere. In the present embodiment, exhaust assembly 41 is provided proximate to sealing assembly 40. Placing the exhaust assembly 41 close the sealing assembly minimizes the deadspace in the breathing circuit.

The present invention contemplates that exhaust assembly 41 can have any configuration, so long as the function of exhausting a sufficient amount of gas to atmosphere is achieved. For example, the exhaust assembly can be configured to provide a continuous flow rate for the venting of exhaust gas to atmosphere, or can be configured to provide a variable flow rate; dependent, for example, on the pressure of the gas in the closed system. In the illustrated embodiment, exhaust assembly 41 is defined by a plurality of vent holes 43 provided in the wall of support member 38. The number, size, hole pattern, and shape of the holes can have any configuration. One example of a multiple-hole type of exhaust assembly suitable for use in the present invention is disclosed in U.S. patent application Ser. No. 10/119,673 filed Apr. 10, 2002 ("the '673 application") and U.S. Publication No. 2003/0005931 published, Jan. 9, 2003. It is to be understood that other types of exhaust assemblies, including those described in the '673 application can be used. It should also be noted that only one exhaust assembly need be provided on the patient interface device, so long as the exhaust flow rate is sufficient to provide an adequate exhaust gas venting function.

A pair of patient contacting members 54 are coupled to frame 36 to support the frame on a patient's face. The patient contacting members are attached to end portions of the frame such that the patient contacting members overlie the user's zygomatic bones, i.e., cheekbones. This location on the face is believed to be a location that is particularly well suited to support the strapping force imposed on the face when the patient interface device is attached on the head. The relatively large size of the patient contacting member, and, in particular, the pad portion of the patient contacting member, help disperse the strapping force of the mask over a wide area on the face.

Patient contacting members 54 include a pad 56 and a pad support 58. Pad 56 can either be permanently or detachably attached to the pad support. If detachable, differently sized or configured pads can be used with the patient interface device to allow a wide variety of customization. It can be appreciated that pad 56 can be attached to pad support 58 in any conventional manner. Pad support 58 is preferably formed from a rigid, lightweight material, such as plastic. Pad support 58 and/or pad 56 also preferably includes a contoured patient contacting surface 60 that is generally concave so that the patient contacting member has a shape that comfortably conforms to the human cheekbone.

Pad 56 is preferably formed from a unitary piece of material, such as silicone, rubber, foam, or gel. However, other materials, in addition to or in place of these materials, can be used. The present invention also contemplates that the pad can be formed from a combination of materials, such as rigid, semi-rigid, and non-rigid materials to provide support where desired. The present invention further contemplates that a removable covering, such as a cloth or fabric slip-cover, can be provided over the pads. Such a covering helps maintain the cleanliness of the pads and increases patient comfort, for example, by allowing moisture under the pad to be absorbed in the covering.

Figure 2:
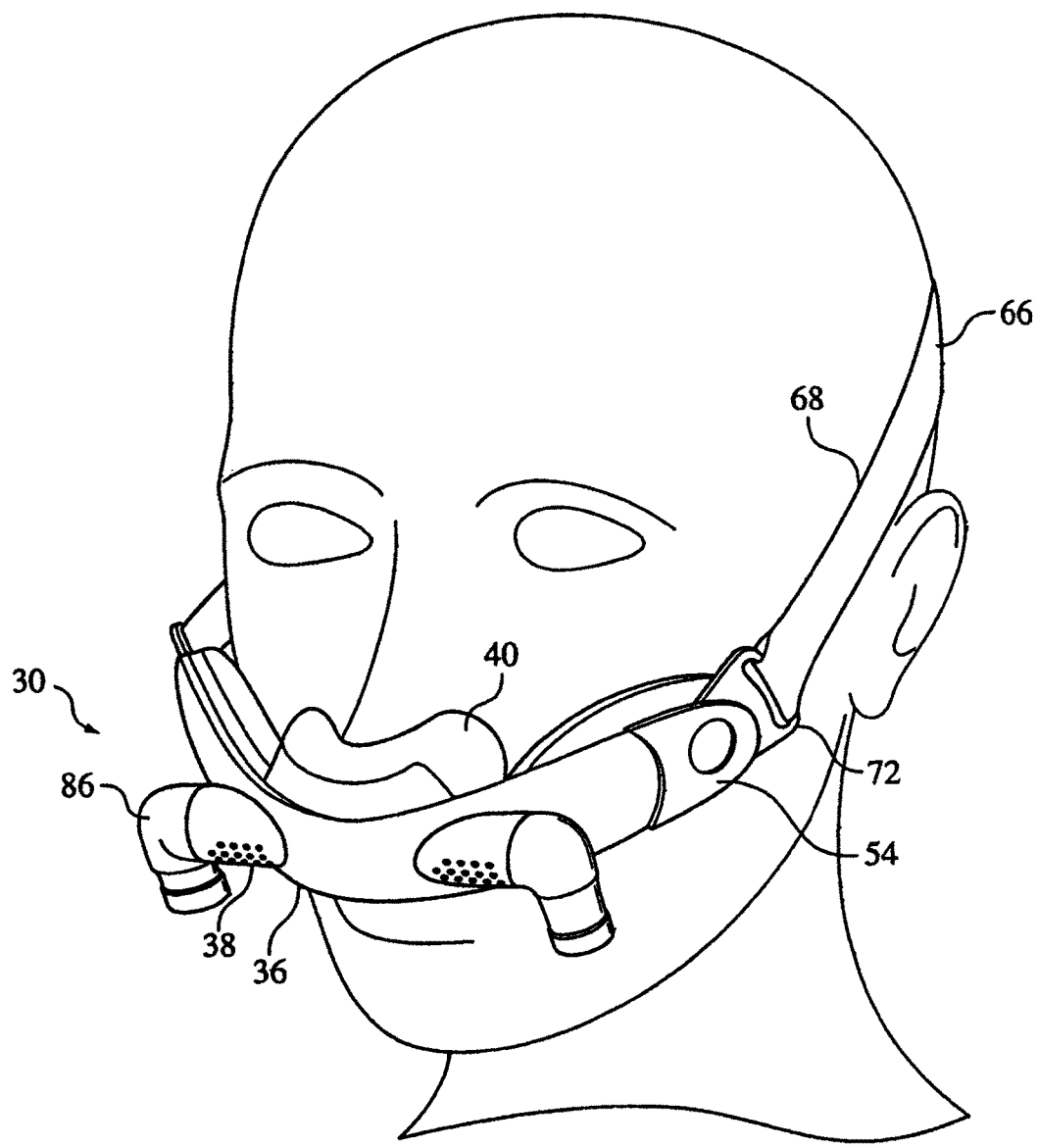
FIG. 2 is a perspective view of the patient interface device of FIG. 1 shown being worn by a patient.

In a preferred embodiment of the present invention, patient contacting members 54 are rotateably attached to frame 36 such that the patient contacting members can rotate relative to the frame, as generally indicated by arrow B in FIG. 1. The rotateable attachment of the patient contacting members to the frame can be accomplished in any conventional manner. The illustrated embodiment, for example, shows a protrusion 62 provided on frame 36 to which the patient contacting members attach. A receptacle 64 is provided in the patient contacting members for engaging and attaching to the protrusion. The movement of the patient contacting members relative to the frame can take place in discrete steps or in a continuous fashion depending on the technique used to rotateably couple the patient contacting members to the frame.

Patient interface device 30 is held on the patient's head by means of a headgear assembly 66. Headgear assembly 66 includes at least one headgear strap 68 that attaches to a headgear attachment portion 70 of patient contacting member 54. Headgear strap 68 is formed from any material sufficiently lightweight and strong to provide the strapping forced need to keep the patient interface device on the user, and is preferably air or gas permeable. A LYCRA® laminated foam and NEOPRENE® are examples of suitable materials for the headgear straps.

In the illustrated embodiment, headgear clips 72 are provided at the ends of the headgear strap to selectively attach the headgear straps to the patient interface device. It is to be understood that a single headgear clip can be provide at one end of the headgear strap, because detaching one end of the headgear strap from the patient interface device should be sufficient to allow the patient interface device to be removed from the patient. The combination of (1) the portion of the headgear attachment portion of patient contacting member and (2) the headgear clips, which cooperate to selectively attach the headgear straps to the patient interface device, are collectively referred to herein as the "headgear attachment assembly."

The length of the headgear strap can be fixed or adjustable. If adjustable, the length can be adjusted using any conventional technique. For example, the present invention contemplates looping a free end of the headgear strap through a slot 74 provided in headgear clip 72. The free end is then attached at any desired location along the length of the headgear strap using any conventional attachment technique, such as a hook and loop fastener, i.e., VELCRO®, or a snap. The free end of the strap that is pulled through the headgear clip to control the overall length of the headgear strap. It is preferable that once the overall length of the headgear strap is adjusted to suit the patient's head, it remains fixed. To make this possible, detachable headgear clip(s) 72 are used to attach the headgear to the headgear attachment portion of the patient contacting member. This avoids the need for the patient to readjust the headgear straps each time the patient interface device is removed.

In the embodiment illustrated in FIGS. 1-3, headgear clip 72 is a generally planar piece of material with a deflectable member 76 protruding slightly therefrom. Headgear attachment portion 70 of patient contacting member 54 includes a receptacle 78 that receives at least a portion of the deflectable member when the headgear clip is fully inserted into a receiving cavity 80 formed in the headgear attachment portion. When the headgear clip is fully inserted into a receiving cavity, the deflectable member 76 moves to its biased position and engages an edge of receptacle 78 such that the headgear clip cannot be pulled out of receiving cavity 80. FIGS. 1 and 2 show the headgear clip inserted into the cavity, and FIG. 3 shows the headgear clip detached from the headgear attachment portion.

In this embodiment, receptacle 78 is a circular opening defined in headgear attachment portion 70 so that deflectable member 76 is exposed when the headgear clip is fully inserted into a receiving cavity. To detach the headgear clip from patient contacting member 54, a force is applied on the exposed portion of the deflectable member causing the edge of the deflectable member to disengage from an edge of receptacle 78, thereby allowing the headgear clip to be slid out of receiving cavity 80. The circular shape of the opening forming receptacle 78 and the complimentary circular shape of deflectable member 76, as well as the relative sizing of these two members, are selected so as to enable the headgear clip to rotate relative to the headgear attachment portion 70, as indicated by arrow C in FIG. 1. Of course, the present invention contemplates that other shapes and configurations for receptacle 78 and deflectable member 76 can be used, including shapes that would prevent such rotational movement of the headgear clip relative to the frame.

As noted above, the flow of gas generated by pressure support system 32 is communicated to patient interface device 30 via patient circuit 34. In the exemplary embodiment, the patient circuit connects to a Y-piece 82, and a pair of hollow leg conduits 84 connect the diverging portions of the Y-piece to elbow couplings 86, which are connected to opposite ends of support member 38. Y-piece 82 can be rigid or non-rigid, and conduits 84 are preferably flexible and lightweight. In the illustrated embodiment, the ends of conduits 84 are press-fit onto coupling portions 88 of elbow couplings 86. This enables the conduits to be detached, if necessary, from the patient interface device.

Elbow couplings 86, are preferably rotateably attached to support member 38 so that each elbow coupling is free to rotate independently on a respective end of the support member, as indicated, for example, by arrow D in FIG. 1. The present invention contemplates that any suitable attachment technique can be used to rotateably attach the elbow couplings to the support member. In the illustrated embodiment, for example, a collar 90 is provided on the end of support member 38 and the elbow coupling includes an attachment portion 92 that rotateably locks onto collar 90.

FIGS. 5-12 illustrate a second embodiment of a patient interface device 100 according to the principles of the present invention. Patient interface device 100 is similar in many respects to patient interface device 30 discussed above. A key difference resides in type of sealing assembly 102 used to communicate a flow of gas from support member 104 to the patient's airway. In the present embodiment, sealing assembly 102 is a nasal-cannula type of patient interface, including a pair of prongs 106 extending from a base portion 108. Openings 110 are provided in prongs 106 to communicate the interior chamber of each prong with a patient's nostril.

It should be noted that the present invention contemplates that the sealing assembly can include other types, styles, sizes, and shapes of patient interface devices in place of the nasal cushion or nasal prongs illustrated and described above. For example, the present invention contemplates providing a sealing assembly that communicates with the nasal passages and the mouth, which is typically referred to as a full-face interface.

It should also be noted that while the sealing assembly is shown above separately attached to the remaining portions of the patient interface device, the present invention contemplates a more permanent coupling between these elements. For example, the sealing assembly can be physically bonded to or integrally formed with the support member. This can be done in any conventional manner. Physically bonding the sealing assembly to the support member can be accomplished by means of a non-detachable mechanical coupling or an adhesive. Integrally forming the sealing assembly with the support member can be accomplished by forming both items from a common material or by two-shot molding this combination of elements. Taking this concept one step further, the present invention contemplates that the entire patient interface device or a subset of the components defining the patient interface device, such as the frame, the support member, and the sealing assembly can be formed as a one-piece structure.

Figure 8:
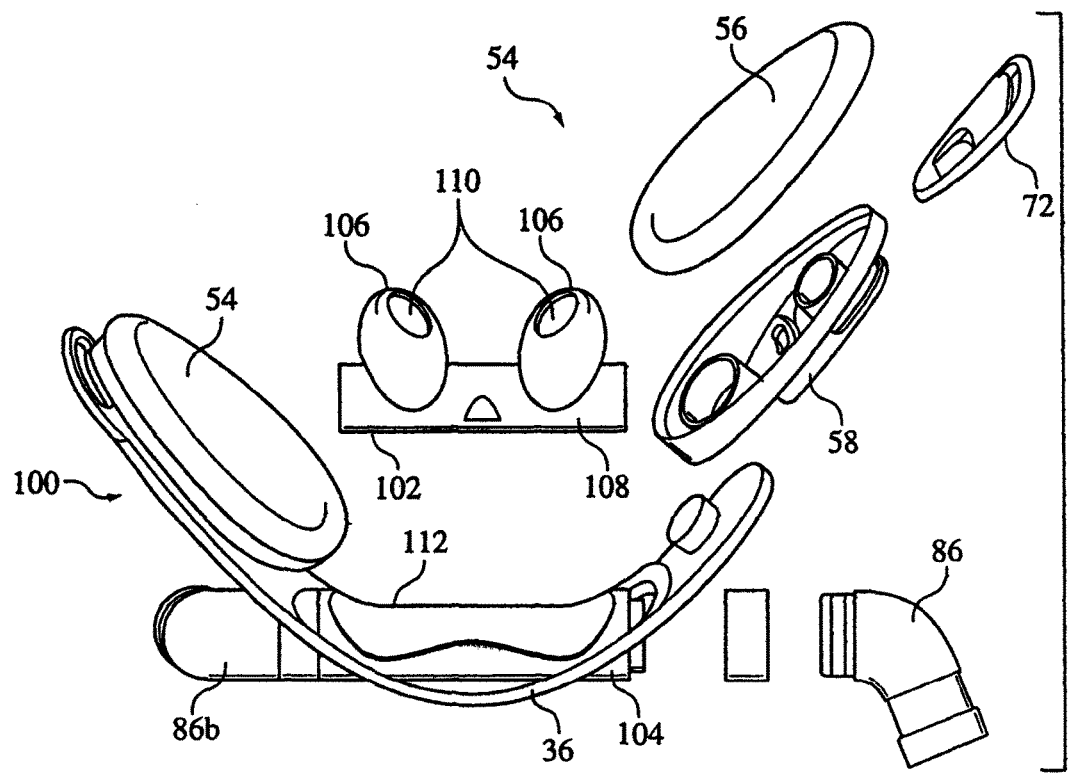
FIG. 8 is an exploded view of the patient interface device of FIG. 5.
Figure 9:
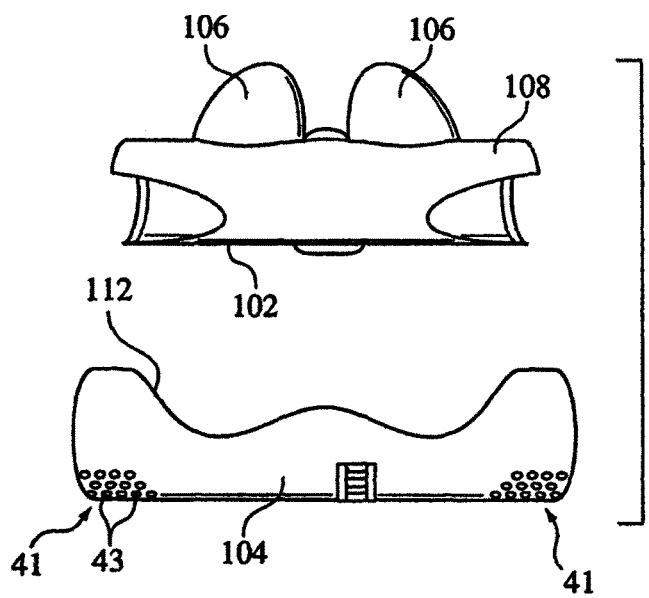
FIG. 9 is an exploded view showing the connection of the sealing assembly to the support member in the patient interface device of FIG. 5.
Figure 10:
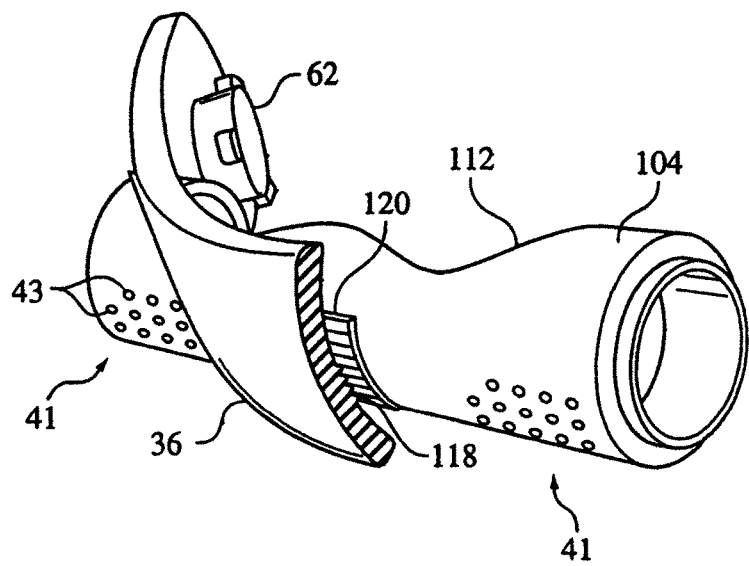
FIG. 10 is a perspective view, partially in section, showing the interaction between the support member and the frame in the patient interface device of FIG. 5.

As perhaps best shown in FIGS. 8 and 9, sealing assembly 102 attaches to support member 104 by being fit into a cutout 112 defined in a wall of the support member. Sealing assembly 102 is configured such that at least base portion 108 is sufficiently flexible that it can be bent, as least slightly, and inserted into cutout 112. The base portion is preferably sized relative to the support member such that the base portion remains engaged within the cutout due to friction between the base portion and the walls of support member 104. An alternative embodiment of the present invention contemplates that base member 108 is relatively rigid, and support member 104 flexes at least slightly, but to a degree sufficient to allow the base member to fit within cutout 112. Yet another embodiment of the present invention contemplates that prongs 106 are removably attached to base member 108. In which case, the base member fits into the support member by removing the prongs from the base member and by removing at least one elbow coupling from the support member. The base member is then slid coaxially into the support member and the prongs and elbow coupling reattached.

As noted above, the present invention contemplates that the elbow couplings are rotateable relative to the support member. The present invention further contemplates that the relative position between the elbow coupling and the support member can be controlled such that the elbow coupling can be located in discrete positions relative to the support member. In one embodiment shown in FIG. 6, a ratchet-type of position control system is used to maintain elbow coupling 86b in a discrete position relative to support member 104. In this embodiment, at least one tooth 114 is provided on elbow coupling 86b and a plurality of tooth engaging members 116 are provided on support member 104. Tooth 114 is moveable between tooth engaging members 116 to select the rotational angle between the elbow coupling and the support member. The tooth and tooth engaging members are sized such that the rotational angle between the elbow coupling and the support member is not easily changed. It should also be understood that the location of the tooth and the tooth engaging members can be reversed from that shown, so that the tooth is provided on the support member and the tooth engaging member is provided on the elbow coupling.

As also noted above, the present invention contemplates that the support member is rotateable relative to the frame. The present invention further contemplates that the relative position between the support member and the frame can be controlled such that the support member can be located in discrete positions relative to the frame. In one embodiment shown in FIGS. 9 and 10, a ratchet-type of position control system is used to maintain support member 104 in a discrete position relative to frame 36. In this embodiment, at least one tooth 118, and preferably a plurality of teeth, are provided on frame 36, and a plurality of engaging members 120 are provided on support member 104. Teeth 118 are moveable along engaging members 120 to select the rotational angle between the frame and the support member. The teeth and tooth engaging members are sized such that the rotational angle between the frame and the support member is not easily changed. It should also be understood that the location of the teeth and the engaging members can be reversed from that shown, so that the teeth are provided on the support member and the engaging member is provided on the frame.

Prongs 106 in patient interface device 100 shown in FIGS. 5-10 are bulbous and shaped to fit comfortably in sealing contact with the area of the nose surrounding each of the patient's nares. Prongs 106 can be formed from any material or combination of materials that is both flexible—to provide a good seal on the patient, and soft—to provide a comfortable patient contacting surface. Examples of materials suitable for use as prongs 106, include, but are not limited to: silicone, rubber, foam, or gel.

Figure 11:
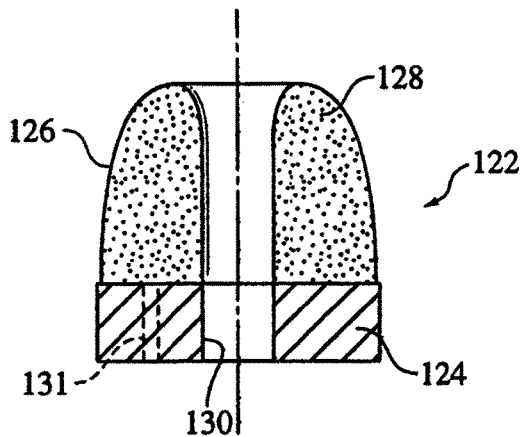
FIG. 11 is a sectional view of a further embodiment for a sealing assembly suitable for use with the patient interface device of the present invention.
Figure 12:
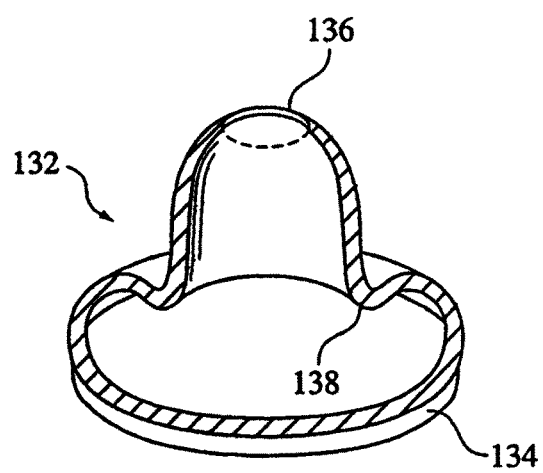
FIG. 12 is a sectional view of a still further embodiment for a sealing assembly suitable for use with the patient interface device of the present invention.

It is to be further understood that the prongs can have other configurations. FIGS. 11 and 12, for example, illustrate further embodiments for the prongs suitable for use with the patient interface device of the present invention. Prong 122 in FIG. 11 includes a base portion 124 that attaches to the support member and an inflatable bladder 126 having an internal chamber 128. A channel 130 defined through the base member and the bladder provides a gas flow path connecting the hollow interior of the support member to the patient's airway. The present invention contemplates that bladder 126 is hollow and permitted to fill with air through a gas flow path 131 when pressure is provided to the patient interface device. This allows the bladder to inflate when the system is pressurized. The present invention also contemplates providing a porous material, such as foam or other particulate matter, within the bladder to give it some degree of structural integrity on its own, rather than relying solely on the inflation of the bladder by the pressure of the gas flow to give the bladder a desired shape.

Prong 132 in FIG. 12, shown partially in cross-section, is defined by a resilient material, such as silicone, and includes a base portion 134 at a proximal end that attaches to the support member. An opening 136 is provided in a distal end of the prong to communicate the hollow interior of the support member with the patient's airway. The wall of the prong between the proximal and distal end portion includes a bend or gusset 138 to allow the distal end of the prong to move or flex in three dimensions. This bending ability allows the distal end of the prong to be self-positioning on the patient when the patient puts on the patient interface device an inserts the prongs into his or her nostrils.

FIGS. 13-24 illustrate various alternative embodiments for headgear attachment assemblies suitable for use with the patient interface device of the present invention. As such, each of the embodiments shown in these figures includes a portion, defined by one or more components, that is a component of the patient contacting member and a portion that corresponds to the headgear clip.

Figure 13:
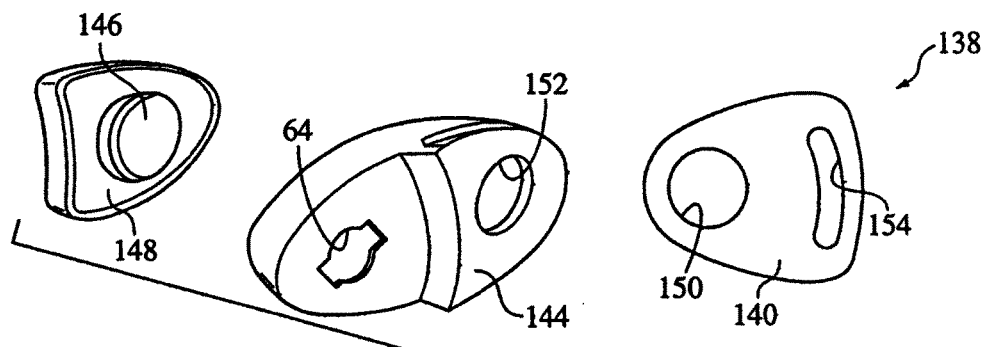
FIG. 13 is a partially exploded view of a first embodiment of a headgear attachment assembly (shown unassembled) suitable for use with the patient interface device of the present invention.
Figure 14:
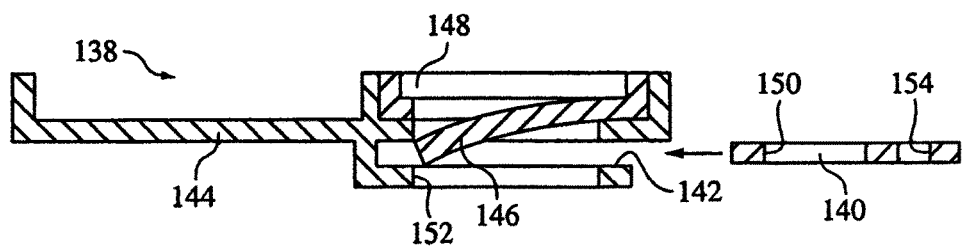
FIG. 14 is a sectional view of the headgear attachment assembly of FIG. 13.

Referring now to FIGS. 13 and 14, there is shown a first embodiment of a headgear attachment assembly 138 (shown unassembled) suitable for use with the patient interface device of the present invention. Headgear attachment assembly 138 includes a headgear clip 140 that inserts into a slot 142 defined in a pad support 144. Headgear clip 140 is held within slot 142 by a biased cantilever member 146 that is attached to an insert 148, which is coupled to pad support 144. More specifically, cantilever member 146 is biased so as to flex into an opening 150 defined in clip 140. As a result, the edge of the cantilever member engages an edge of the opening. The circular shape of biased cantilever member 146 and opening 150, and the relative size of the headgear clip and slot 142, allow the headgear clip to swivel or rotate within the slot while the clip is engaged with the pad support.

To release the clip from the pad support, cantilever member 146 must be deflected away from the headgear clip so that the clip disengages from the cantilever member and is free to slide out of slot 142. An opening 152 is provided in an exposed surface of pad support 144 to allow access to cantilever member 146 to apply a deflecting force on the arm against the bias force. A slot 154 is provided on clip 140 to attach the headgear to the clip. It is to be understood that a main feature of this embodiment is to provide a biased cantilever member associated with the pad support. Although a separate insert 148 that attaches to the pad support is used to provide this feature in this embodiment, the biased cantilever member can be formed in other ways, with or without being a separate component.

Figure 15:
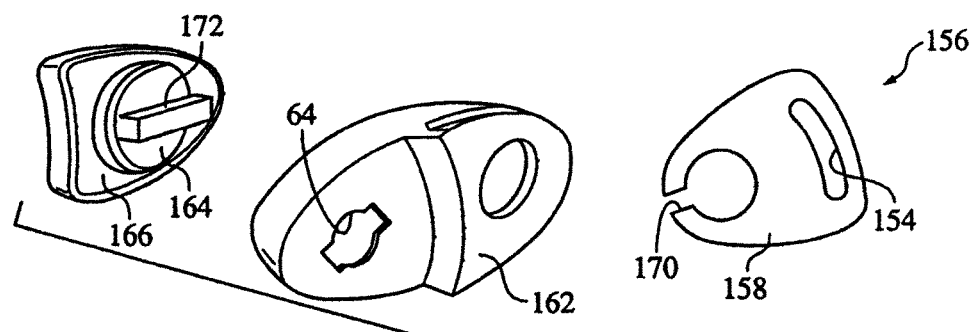
FIG. 15 is a partially exploded view of a second embodiment of a headgear attachment assembly (shown unassembled) suitable for use with the patient interface device of the present invention.
Figure 16:
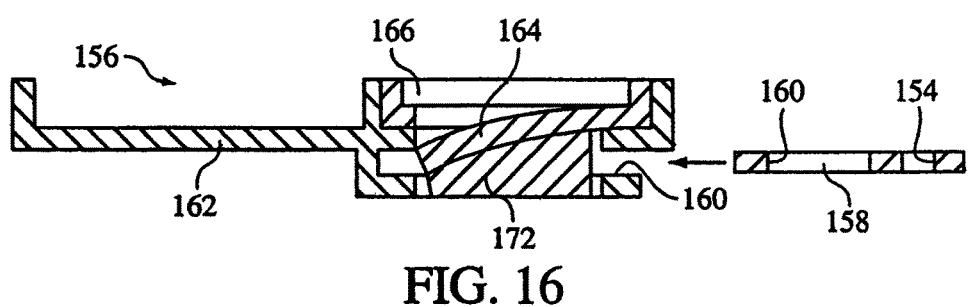
FIG. 16 is a sectional view of the headgear attachment assembly of FIG. 15.

FIGS. 15 and 16 illustrate a second embodiment of a headgear attachment assembly 156 (shown unassembled) suitable for use with the patient interface device of the present invention. As in the previous embodiment, headgear attachment assembly 156 includes a headgear clip 158 that inserts into a slot 160 defined in a pad support 162 and is held in the slot by a biased cantilever member 164 attached to an insert 166 that engages an opening 168 defined in the clip. A unique feature of this design is that a slot 170 is added to headgear clip 158 and a key 172 is added to biased cantilever member 164 so that a "slot-and-key" configuration is formed, with slot 170 inserting into key 172. Unlike the prior embodiment, this design prevents movement of the headgear clip in the pad support. It can thus be appreciated that if rotational movement is desired, insert 148 is coupled to pad support 162, and if no rotation is desired, insert 166 is used.

Figure 17:
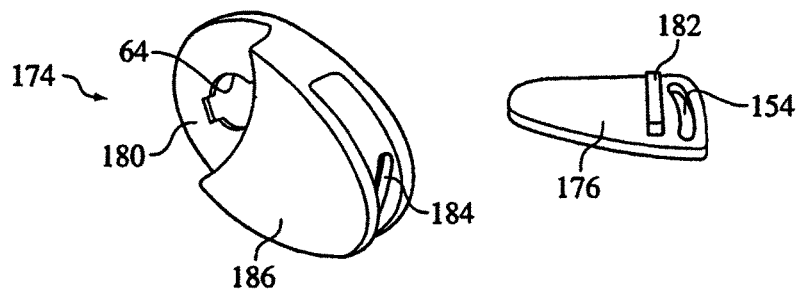
FIG. 17 is a perspective view of a third embodiment of a headgear attachment assembly (shown unassembled) suitable for use with the patient interface device of the present invention.
Figure 18:
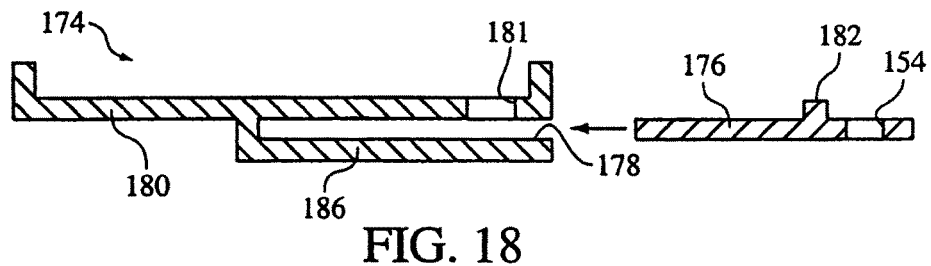
FIG. 18 is a sectional view of the headgear attachment assembly of FIG. 17.

FIGS. 17 and 18 show a third embodiment of a headgear attachment assembly 174 (shown unassembled) suitable for use with the patient interface device of the present invention. Headgear attachment assembly 174 includes a headgear clip 176 that inserts into a slot 178 defined in a pad support 180. Headgear clip 176 includes a tab 182 that inserts into a slot 184 provided in pad support 180. A cover member 186 on pad support 180 deflects slightly to allow the clip to insert and engage within the slot in the pad support. Cover member 186 holds the headgear clip such that tab 182 remains engaged in slot 184. To detach the headgear clip from the pad support, a slight deflecting force is applied to cover member 186, for example, by pulling away from the patient on the exposed end of the headgear clip. The force deflects the cover member outward, widening slot 184, so that tab 182 can disengage from the slot.

Figure 19:
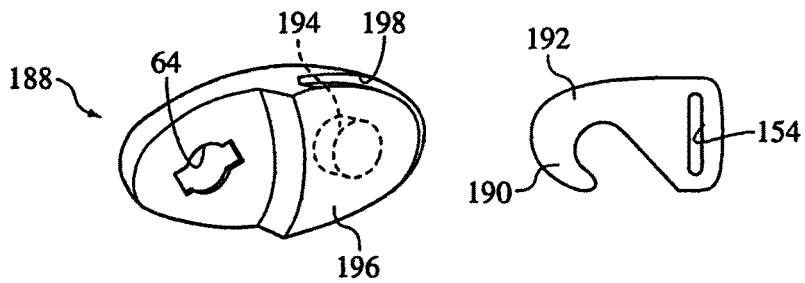
FIG. 19 is a perspective view of a fourth embodiment of a headgear attachment assembly (shown unassembled) suitable for use with the patient interface device of the present invention.
Figure 20:
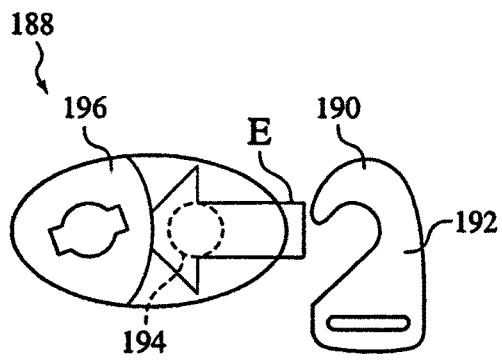
FIGS. 20 and 21 are side views showing the coupling operation of the headgear assembly of FIG. 19.
Figure 21:
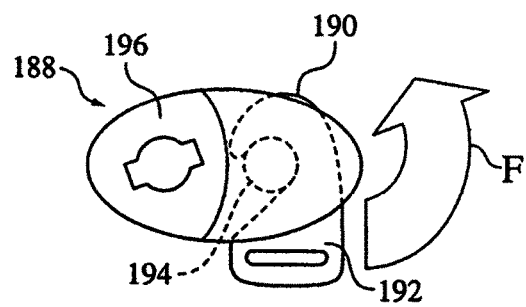

FIGS. 19-21 illustrate a fourth embodiment of a headgear attachment assembly 188 suitable for use with the patient interface device of the present invention. In this embodiment, a hook 190 is provided on headgear clip 192. Hook 190 grapples a pin 194 on pad support 196. Attaching hook 190 to pin 194 in this exemplary embodiment involves positioning headgear clip 192 at an generally 90° angle relative to pad support 196 and inserting the hook into a slot 198 defined in the pad support, as indicated by arrow E in FIG. 20. Once inserted, headgear clip 192 is rotated, as indicated by arrow F in FIG. 21, back into alignment with the pad support, thereby attaching the hook onto the pin.

Figure 22:
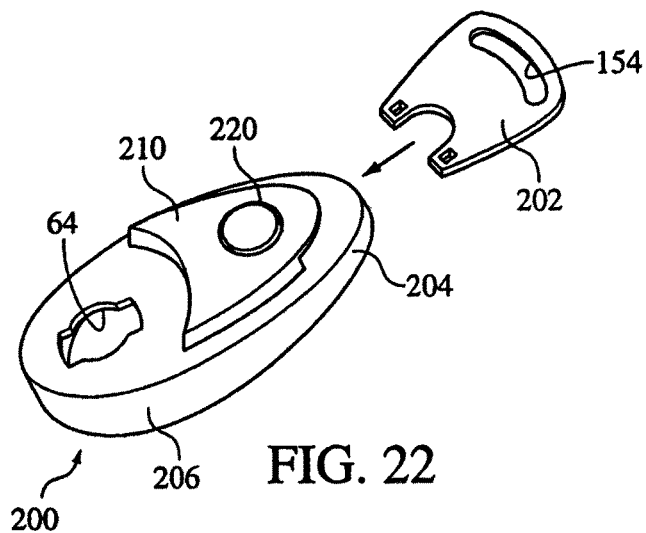
FIG. 22 is a front perspective view of a fifth embodiment of a headgear attachment assembly (shown unassembled) suitable for use with the patient interface device of the present invention.
Figure 23:
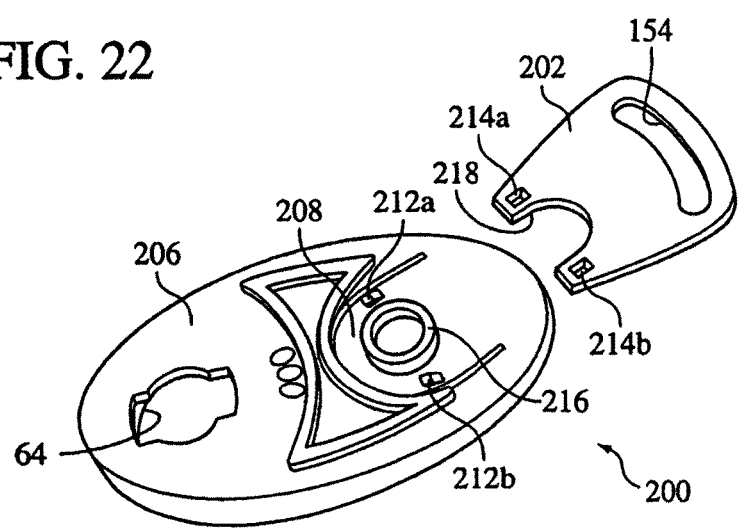
FIG. 23 is a perspective view of the headgear attachment assembly of FIG. 22 with the cover portion removed.
Figure 24:
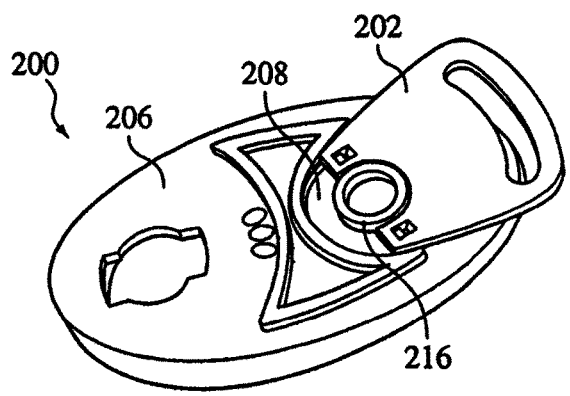
FIG. 24 is a perspective view of the headgear attachment assembly of FIG. 22 shown assembled.

A fifth embodiment of a headgear attachment assembly 200 suitable for use with the patient interface device of the present invention is shown in FIGS. 22-24. Headgear attachment assembly 200 includes a headgear clip 202 that inserts into a slot 204 defined in a headgear clip 206. Headgear clip 202 is held within slot 204 by a biased cantilever member 208 coupled to pad support 206. FIG. 22 shows a cover member 210 coupled to pad support 206 such that slot 214 is defined between the cover member and the main body of the pad support. FIGS. 23 and 24 show the pad support with the cover member removed, revealing biased cantilever member 208.

A pair of protrusions 212*a* and 212*b* are provided on cantilever member 208, and a corresponding pair of slots 214*a* and 214*b* are provided on headgear clip 202. A central protrusion 216 is also provided on cantilever member 208, and a similarly shaped cutout 218 is defined in headgear clip 202 so that the headgear clip nests against the central protrusion. Preferably a cap 220 is provided over protrusion 216.

Headgear clip 202 attaches to pad support 206 by inserting the headgear clip into slot 214 as shown in FIGS. 22-24. During insertion, cantilever member 208 deflects away from the headgear clip as the end of the headgear clip begins to engage protrusion 212*a* and 212*b*. When fully inserted, the bias force on cantilever member 208 urges protrusion 212*a* and 212*b* into slots 214*a* and 214*b*, as shown in FIG. 24. The engagement of the protrusions within the slots maintains the headgear clip locked onto the pad support.

To release the headgear clip from the pad support, the user manually moves protrusion 212*a* and 212*b* out of engagement with slots 214*a* and 214*b* by pressing on cap 220. The force on cap 220, and, consequently on protrusion 216 and the distal end of the cantilever member, causes the cantilever member to deflect away from the headgear clip, releasing the clip from the pad support.

Figure 25A:
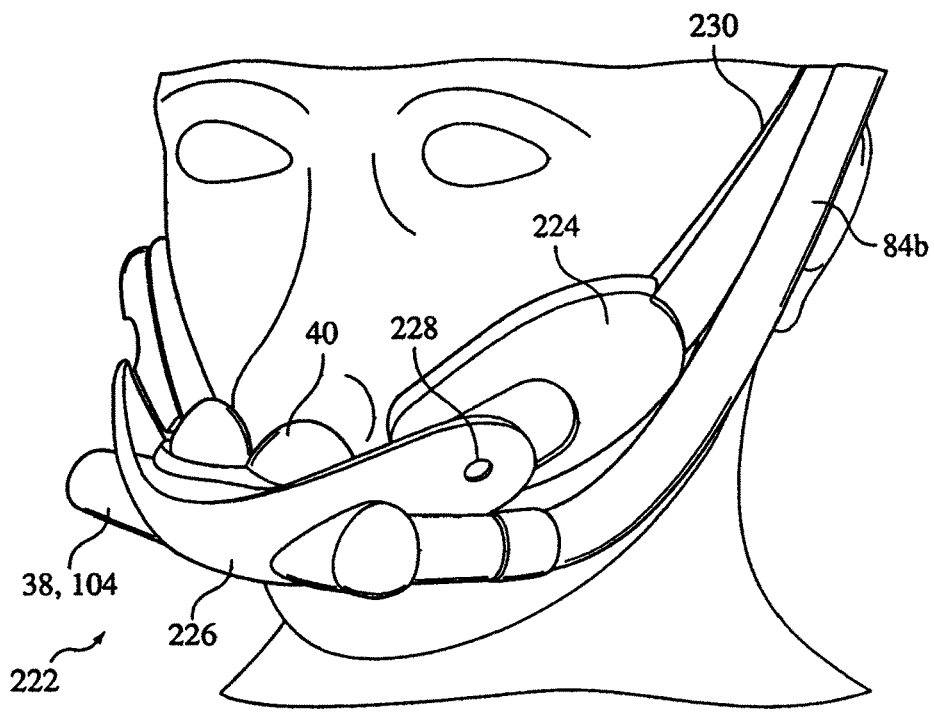
FIGS. 25A and 25B are perspective and side views, respectively, of a third embodiment of a patient interface device according to the principles of the present invention.
Figure 25B:
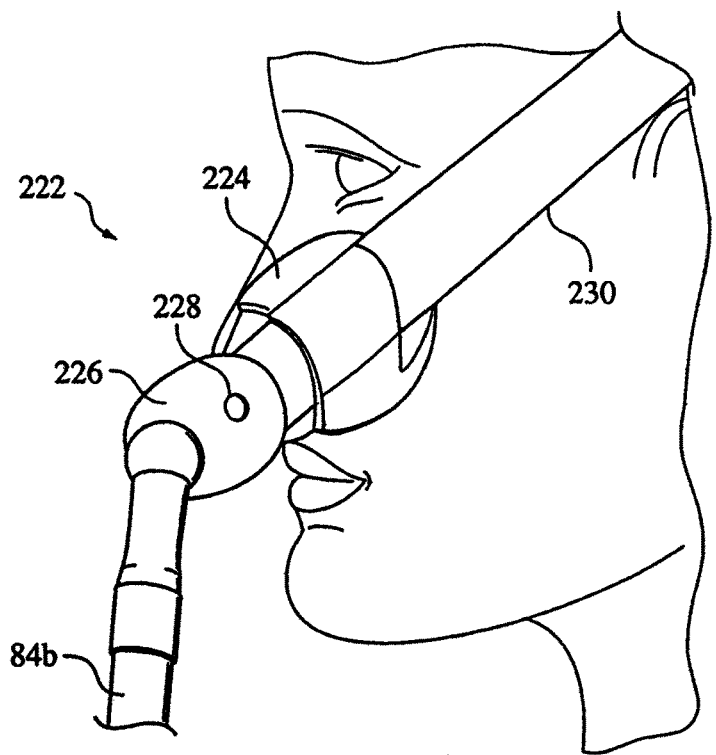

A third embodiment of a patient interface device 222 according to the principles of the present invention is shown in FIGS. 25A and 25B. Patient interface device 222 is generally similar to that shown in FIGS. 1-10 except for the configuration for the pad support and headgear attachment. It should be noted that while FIGS. 25A and 25B show a nasal cannula type of sealing assembly 40, any conventional sealing assembly can be used with this patient interface device, including those discussed above.

In this embodiment, a patient contacting member 224 is attached to frame 226 at an attachment point 228. It should be noted that patient contacting member 224 can have a variety of configurations, and a similar shaped contacting member is provided on the other side of the frame. An end of a headgear strap 230 is also attached to the frame at attachment point 228. Preferably, the patient contacting member and the headgear are rotateably attached to the frame so that both rotate or swivel with respect to the frame. In the illustrated embodiment, a slot is provided in the pad support portion of the patient contacting member, and the headgear strap is inserted into this slot so that the patient contacting member and the headgear strap are aligned with one another. The present invention also contemplates allowing the headgear strap and the patient contacting member to move independently, for example, by eliminating the slot in the pad support or by avoiding passing the headgear strap through such a slot.

Figure 26B:
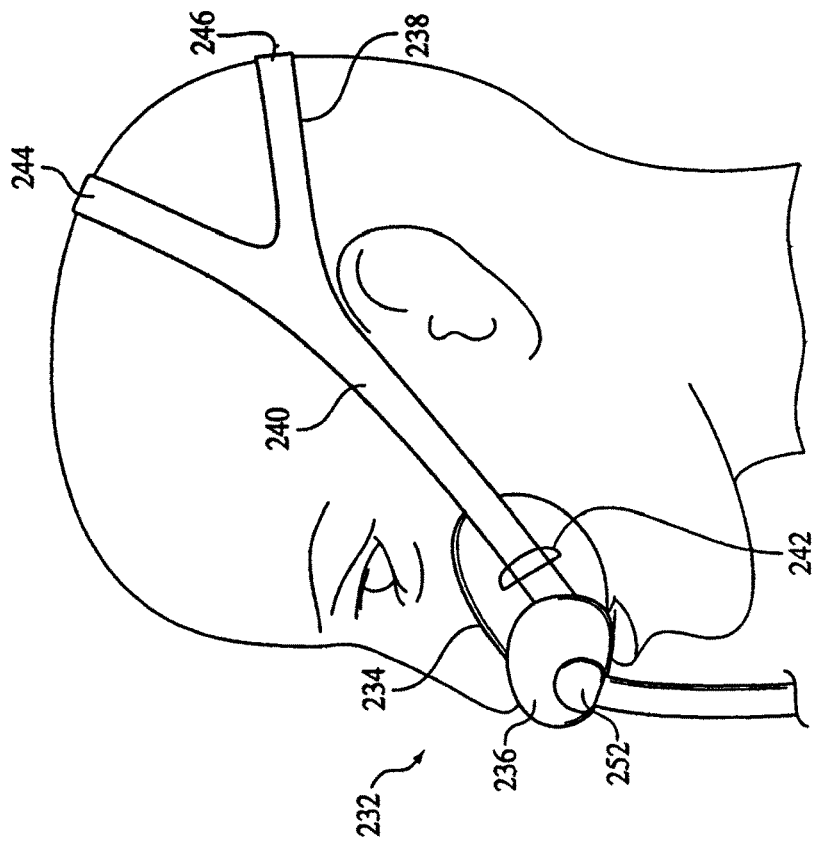
FIGS. 26A and 26B are perspective and side views, respectively, of a fourth embodiment of a patient interface device according to the principles of the present invention.
Figure 26A:
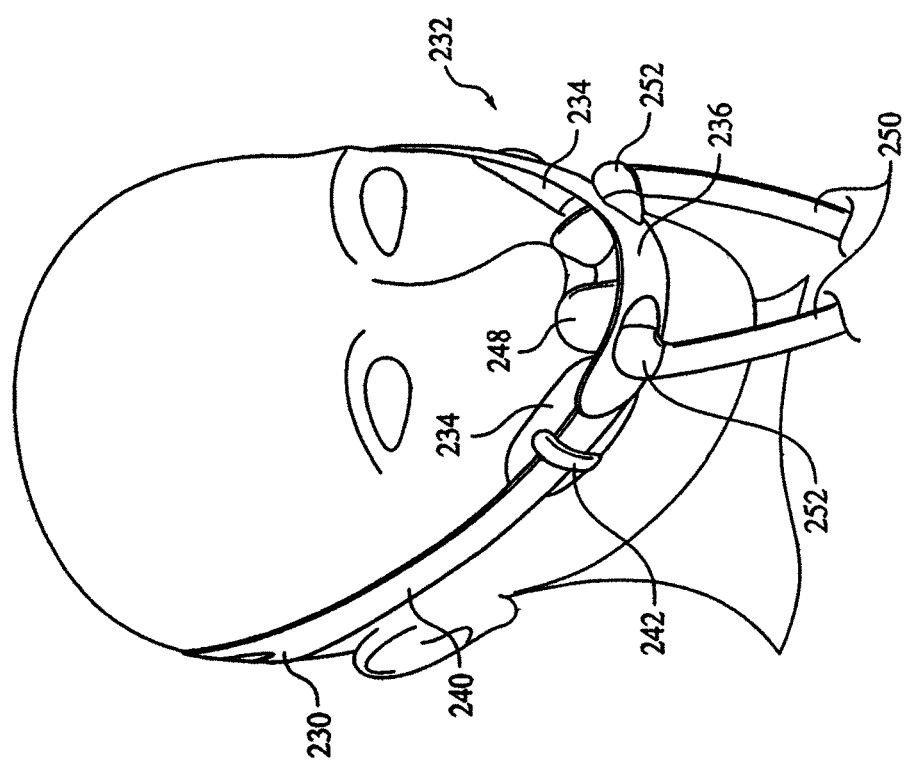
Figure 27A:
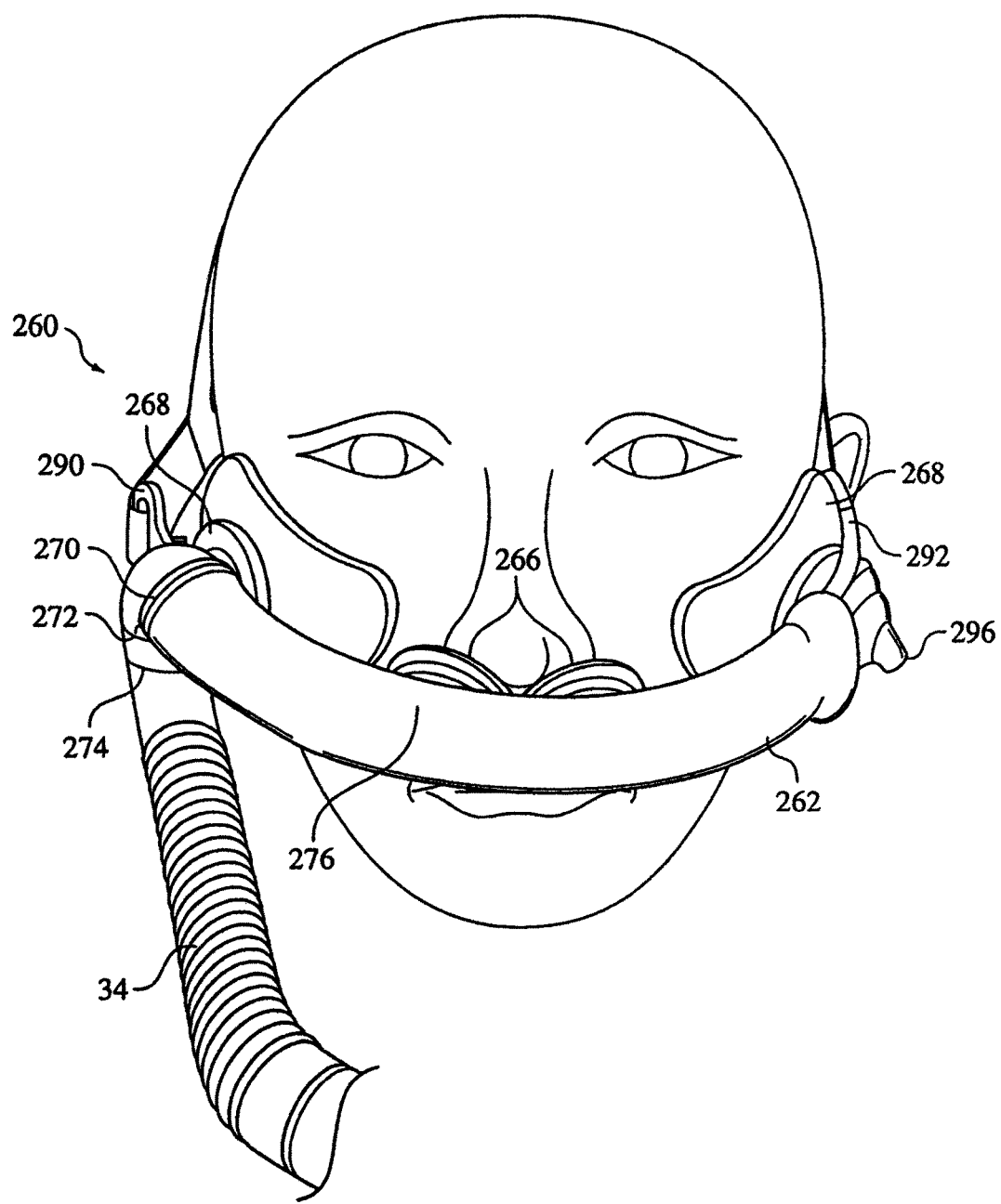
FIGS. 27A-27C are front and perspective views of a fifth embodiment of a patient interface device according to the principles of the present invention shown on a patient.
Figure 27C:
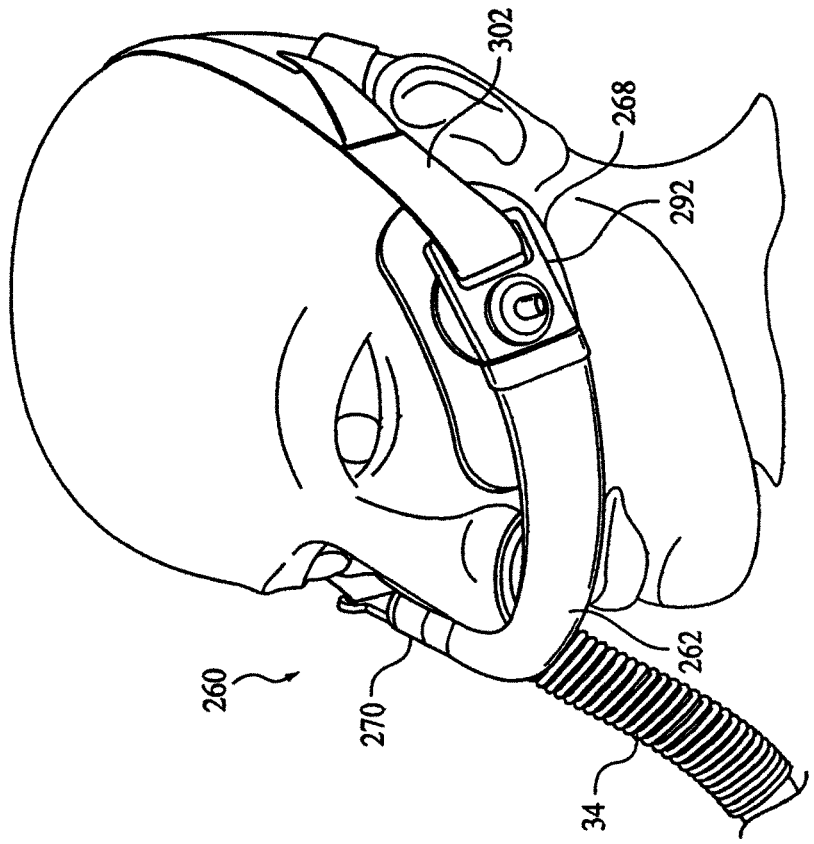
Figure 27B:
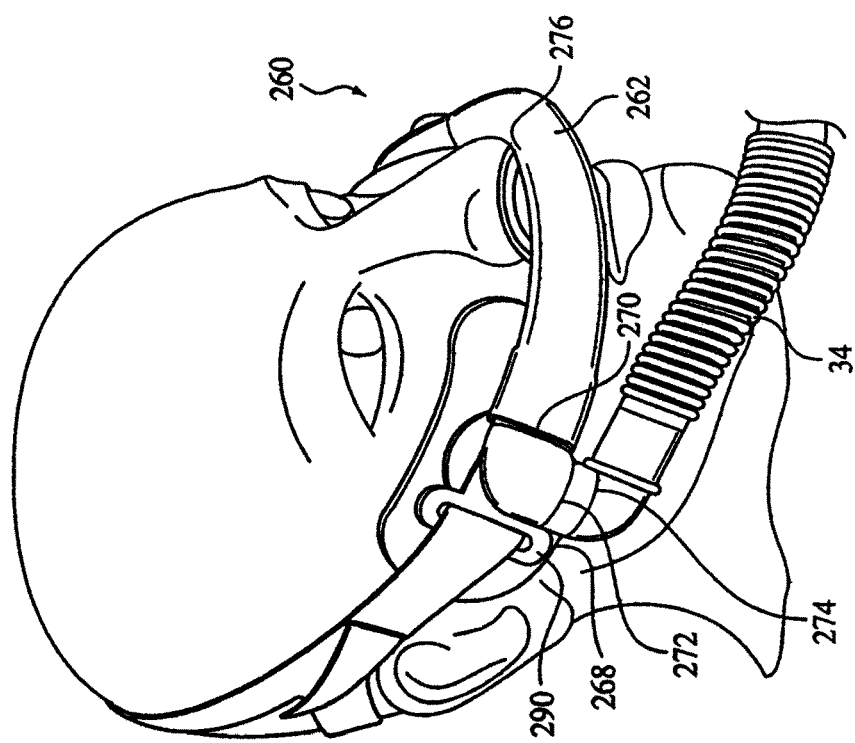
Figure 28:
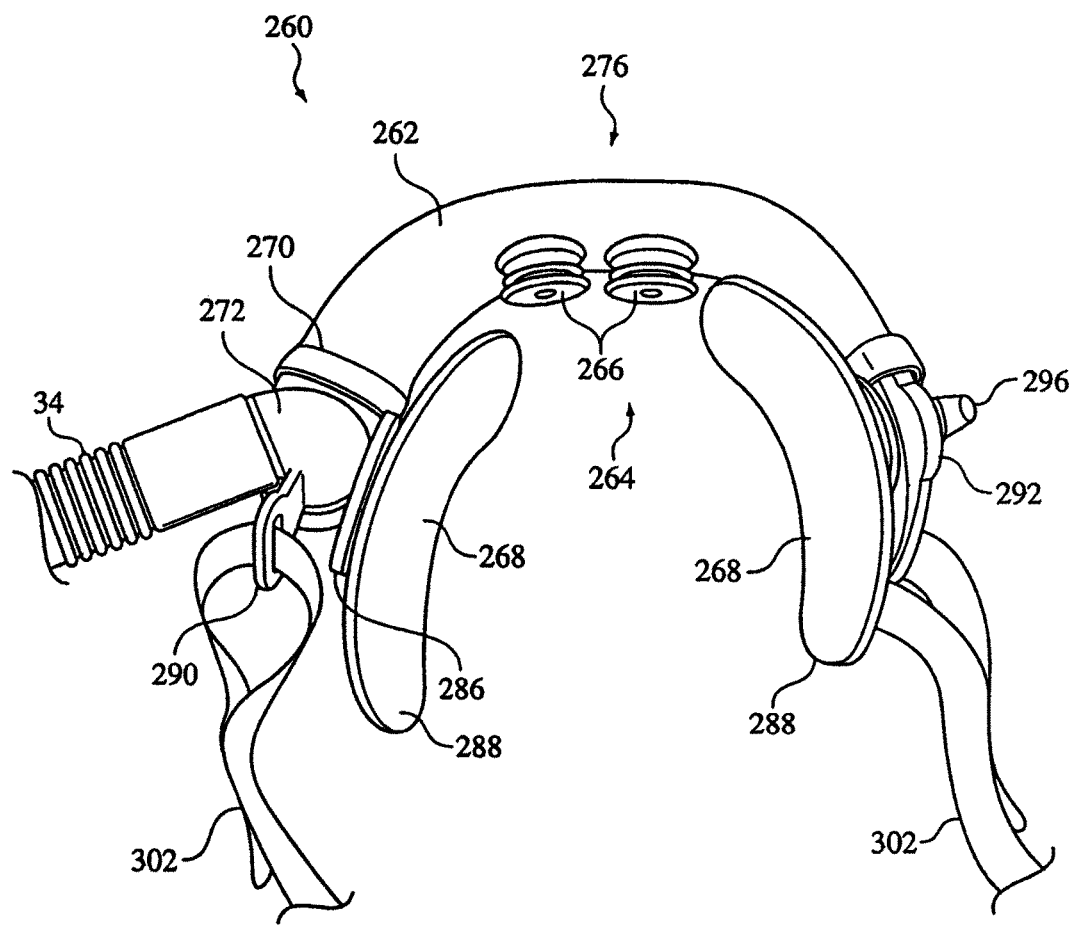
FIG. 28 is a bottom view of the patient interface device of FIGS. 27A-27C.
Figure 29:
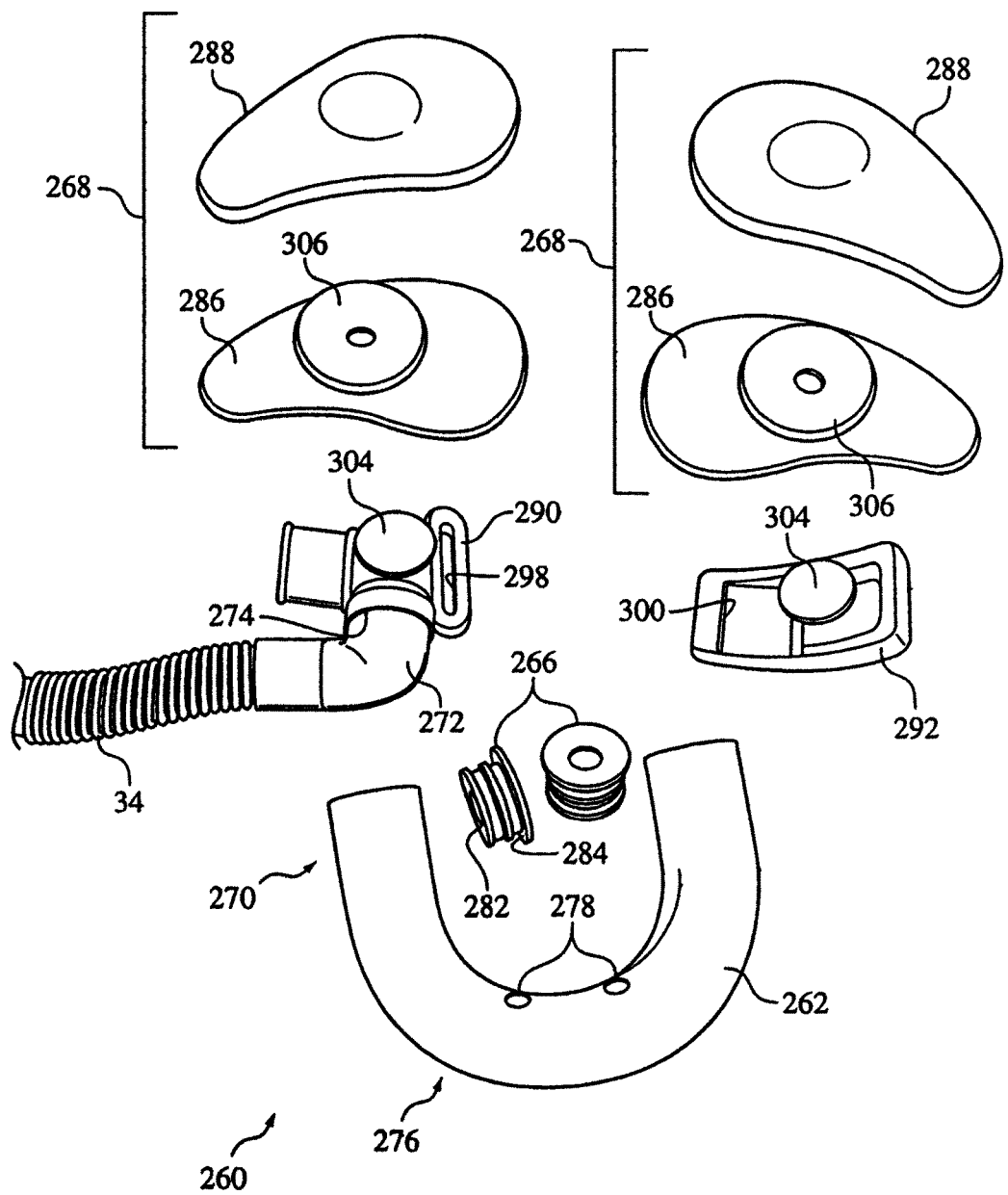
FIG. 29 is an exploded view of the patient interface device of FIGS. 27A-27C.
Figure 30:
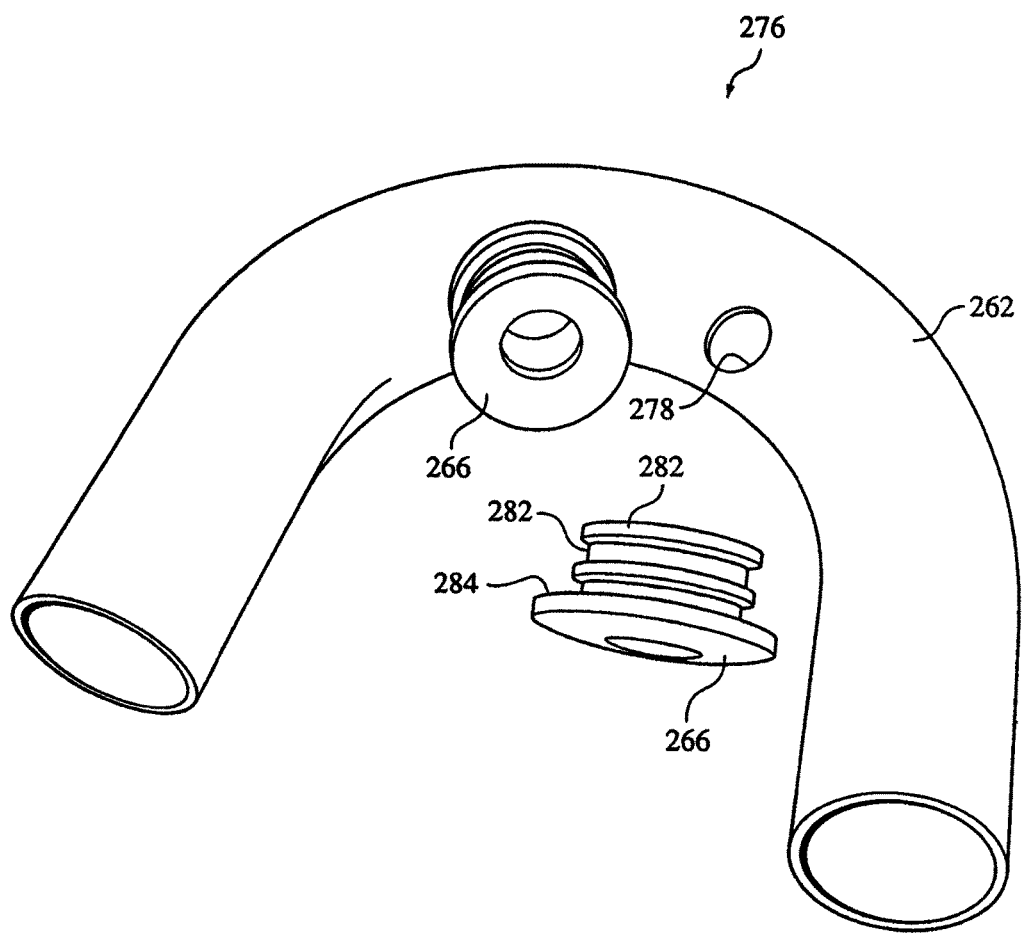
FIG. 30 is a detailed view of the nasal prongs and support member in the patient interface device of FIGS. 27A-27C.

FIGS. 26A and 26B illustrate a fourth embodiment of a patient interface device 232 according to the principles of the present invention. Patient interface device 232 is generally similar to that shown in FIGS. 1-10 and 25A-25B, except for the configuration for the pad support and the attachment of the sealing assembly to the frame. It should be noted that while FIGS. 26A and 26B show a nasal cannula type of sealing assembly 40, any conventional sealing assembly can be used with this patient interface device, including those discussed above.

Patient interface device 232 includes patient contacting members 234 that are attached to frame 236. In this embodiment, the patient contacting members are the pads themselves, i.e., the pad supports present in the previous embodiments have been eliminated in favor of connecting the pads directly to the frame. The pads are either fixed in position on the frame or rotateably attached thereto. A headgear 238, including headgear straps 240, is attached to the patient interface device in either a fixed or rotateable fashion. In the illustrated embodiment, headgear straps 240 are connected to patient contacting members 234 via a loop 242. Alternatively, the present invention contemplates not attaching the headgear straps to the patient contacting members, so that each is independent of the other. Headgear 238 includes an upper strap 244 and a lower strap 246 generally located at the back of the patient's head. This configuration maximizes the stability of the headgear.

Unlike the previous embodiment, in this embodiment there is no support member to which the sealing assembly is attached. Instead, a sealing assembly 248 is attached directly to one side of frame 236. Sealing assembly 248 corresponds to sealing assembly 40, except that sealing assembly 248 is attached to the frame, not support member 38 or 104. Conduits 250 are coupled to the other side of the frame such that the flow of gas provided by these conduits is delivered to the interior of sealing assembly 248. In the illustrated exemplary embodiment, an elbow coupling 252 is provided at the end of each conduit 250 to rotateably connect each conduit to the frame. It is to be understood that the connection of conduit 250 to frame 236 can be done without the elbow coupling, and can be a fixed connection rather than being rotateable. In addition, the rotational angle between the conduit and the frame can be controlled so that the conduit can be placed in discrete angular positions relative to the frame. See, e.g., FIG. 6 and the associated text describing this figure.

Reference will now be made to FIGS. 27A-30, which show a fifth embodiment of a patient interface device 260 according to the principles of the present invention shown on a patient. Patient interface device 260 includes a support member 262 that supports a sealing assembly 264, which, in the illustrated embodiment, is a pair of nasal prongs 266. Unlike the previous embodiments, patient interface device 260 does not include a frame to which the support member is attached. Instead, support member 262 spans the user's face generally below the eyes and is supported directly on the face by patient contacting members 268. Support member 262 is preferably formed from a semi-rigid material such that it is sufficiently strong to support the sealing assembly 264, yet flexible enough to fit a variety of differently sized patients. An example of a suitable material is silicone that is either thick enough to provide the necessary support or reinforced.

Support member 262 includes a conduit coupling portion 270 to which a patient circuit 34 is attached. Preferably, a coupling assembly 272 is provided at conduit coupling portion 270 to couple the patient circuit to the support member in a rotateable fashion. In the illustrated embodiment, coupling assembly 272 is a U-shaped conduit having an upper portion and a lower portion. The present invention contemplates providing a swivel joint 274 in coupling assembly 272 so that the upper portion of coupling assembly 272 rotates relative to the lower portion. It is to be understood that other rotateable couplings can be provided to connect the patient circuit to the support member. For example, the present invention contemplates coupling an end of a patient circuit to a lower portion of coupling assembly 272 in a rotateable fashion.

Support member 262 includes a sealing assembly coupling portion 276 to which sealing assembly 264 is attached. Support member 262 includes a hollow interior that communicates conduit coupling portion 270 with sealing assembly coupling portion 276. In the illustrated embodiment, sealing assembly coupling portion 276 includes a pair of openings 278 defined in a wall of the support member to which prongs 266 are attached. Nasal prongs 266 include a mounting portion 280, which in the illustrated embodiment is a flange that inserts into opening 278. The edge of opening 278 is seated in a groove 282 next to the flange. A patient contacting flange 284 is provided at an opposite end of prongs 266 to rest against the patient's nose around the nares. A gas flow path is defined through each prong to communicate the patient's airway with the interior of support member 262.

The present invention contemplates that sealing assembly coupling portion 276 can be configured to couple any one of a variety of different types of sealing assemblies to the support member. For example, the nasal cushion type of interface shown in FIG. 1 can be provided on support member 262. It to be understood that the nasal cannula type of patient interface can have other configurations, sizes, and styles as discussed above.

As noted above, patient contacting members 268 are coupled to opposite ends of support member 262. Patient contacting members 268 include a pad support 286 that is coupled to the support member. Pad support 286 is rigid or semi-rigid and is preferably shaped to provide a comfortable contact with the patient's face, for example, by having a concave patient contacting surface. A pad 288 is coupled to pad support 286 in any conventional manner. In the illustrated embodiment, pad 288 is shaped like a sleeve to fit over pad support 286. This configuration for the patient contacting member allows easy replacement and cleaning of the pad.

A pair of headgear attachment assemblies 290 and 292 are provided on each end of the support member. In the illustrated embodiment, headgear attachment assembly 290 is coupled to coupling assembly 272, and headgear attachment assembly 292 is provided at an end 294 of support member 262. Because support member 262 is a generally tubular structure in the illustrated embodiment, headgear attachment assembly 292 also serves to seal end 294 of support member 262 and provides an exhaust assembly 296. In the illustrated embodiment, exhaust assembly 296 is a single port that is continuously open to allow a continuous flow of gas to the ambient atmosphere. It is to be understood that exhaust assembly 296 can have any configuration, including those described above. Each headgear attachment assembly 290 and 292 includes a slot 298 and 300, respectively, to which a headgear strap 302 is connected.

By providing conduit coupling 270 at one end of support member 262, and exhaust assembly 296 at the other, a continuous flow of gas is maintained from the one side of the structure to the other. By having this continuous flow directed past the nasal prongs, rebreathing of exhaled $CO_2$ by the patient is drastically reduced, if not eliminated.

Patient contacting members 268 are coupled to headgear attachment assembly 292 and to coupling assembly 272. Preferably, patient contacting members 268 are rotateably coupled to headgear attachment assembly 292 and to coupling assembly 272. A first mounting member 304 is provided on headgear attachment assembly 292 and coupling assembly 272. A second mounting member 306 is provided on pad support 286. First mounting member 304 is preferably rotateably coupled to second mounting member 306 such that the patient contacting members rotate or swivel with respect to support member 262.

Figure 31A:
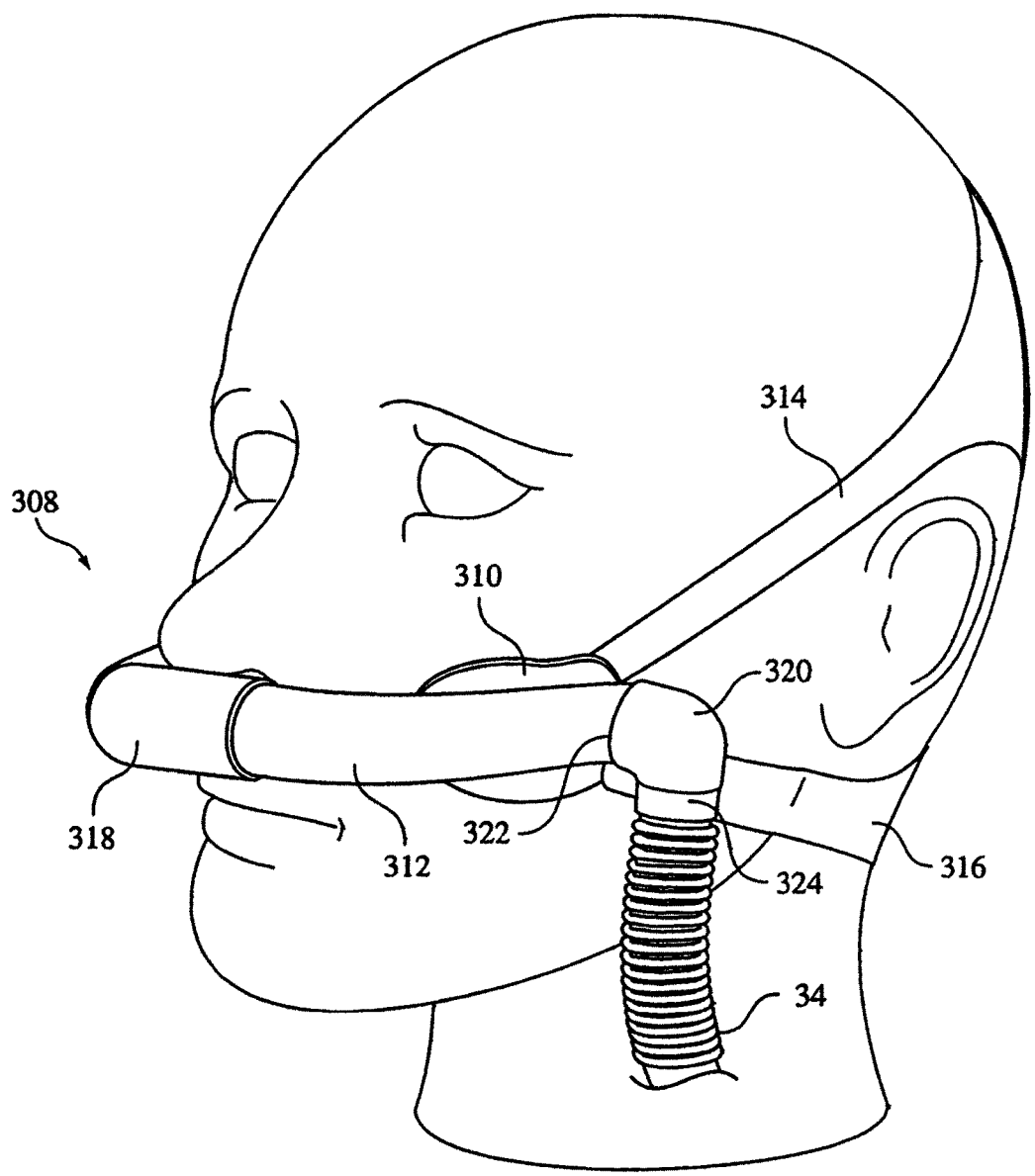
FIG. 31A-31C are a perspective, front, and side views, respectively, of a sixth embodiment of a patient interface device according to the principles of the present invention shown on a patient.
Figure 31C:
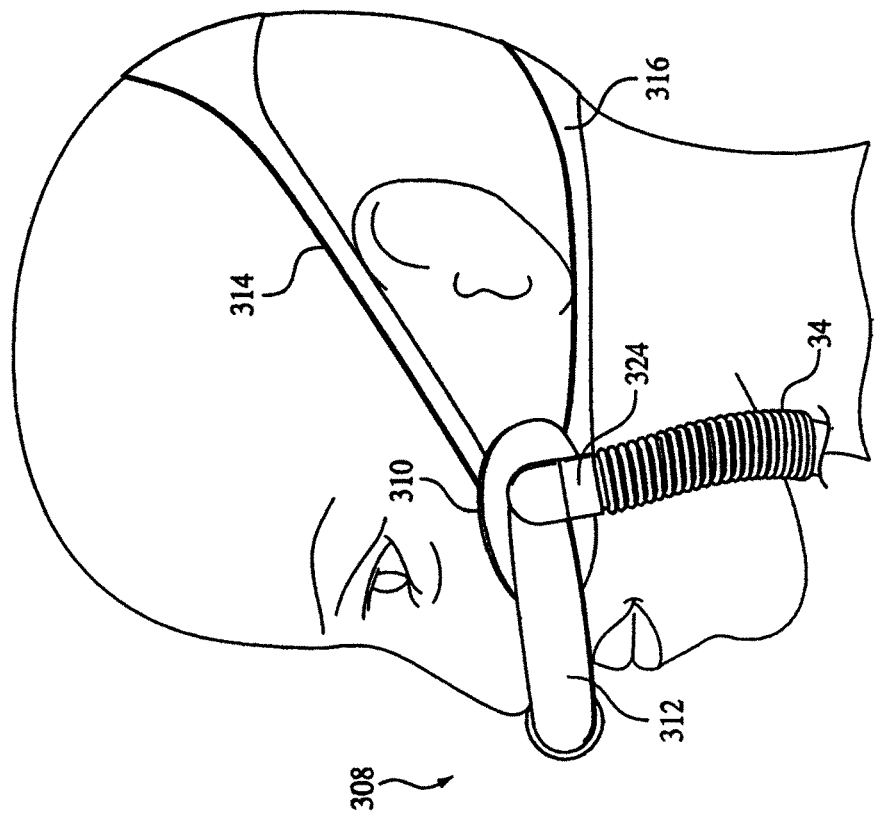
Figure 31B:
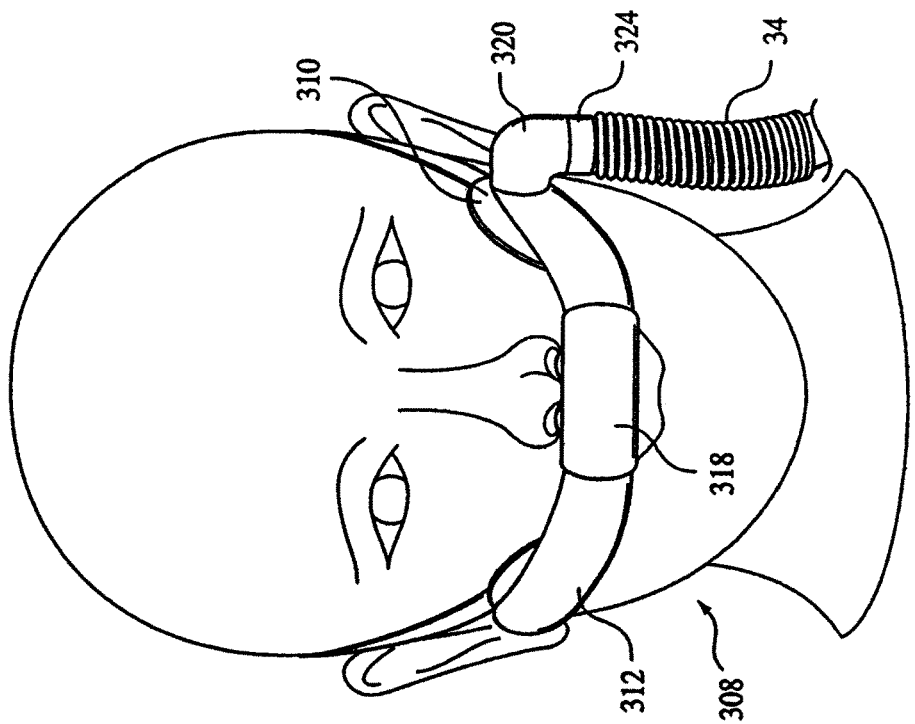

FIG. 31A-31C illustrate a sixth embodiment of a patient interface device 308 according to the principles of the present invention shown on a patient. Patient interface device 308 is generally similar to that shown in FIGS. 27A-30 except that patient contacting members 310 are coupled directly to a support member 312 in a fixed position, i.e., the patient contacting members do not rotate relative to the support member. A pair of headgear straps 314 and 316 are coupled to patient contacting members 310.

A sealing assembly support 318 is coupled to support member 312 and supports a sealing assembly, which is either a nasal cannula type interface (as shown) or a sealing cushion. Sealing assembly support 318 is preferably rotateably coupled to support member 312 so that the patient can control the position of the sealing assembly relative to the support member. An elbow coupling 320 is provided at an end portion of support member 312 to couple patient circuit 34 to the support member. Preferably a joint 322 between the elbow coupling and the support member and a joint 324 between the patient circuit and the elbow coupling are swivel joints to allow rotational movement between the two members being joined.

Figure 32B:
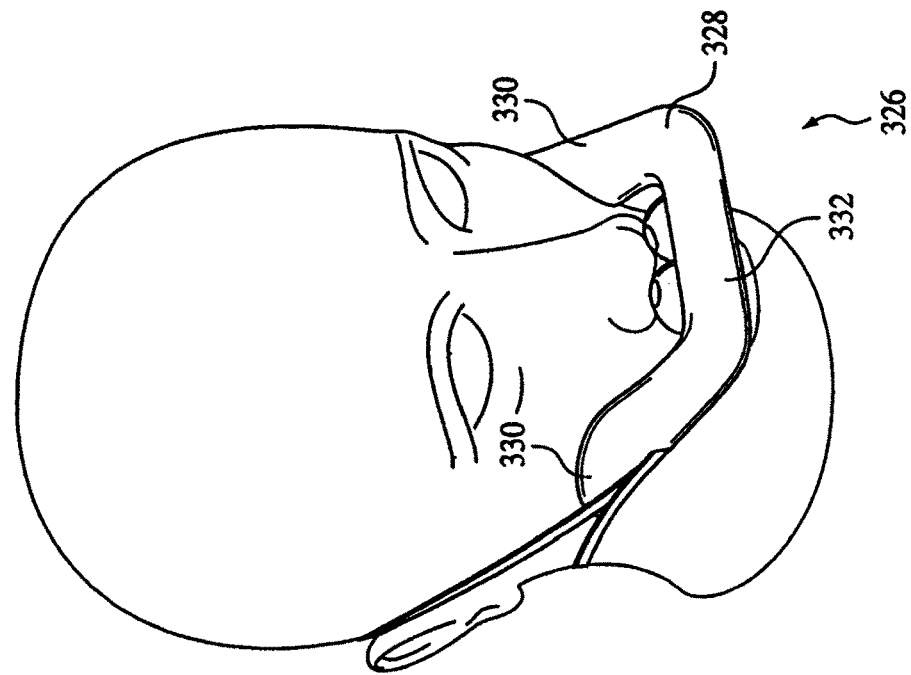
FIGS. 32A and 32B are perspective views of a seventh embodiment of a patient interface device according to the principles of the present invention shown on a patient.
Figure 32A:
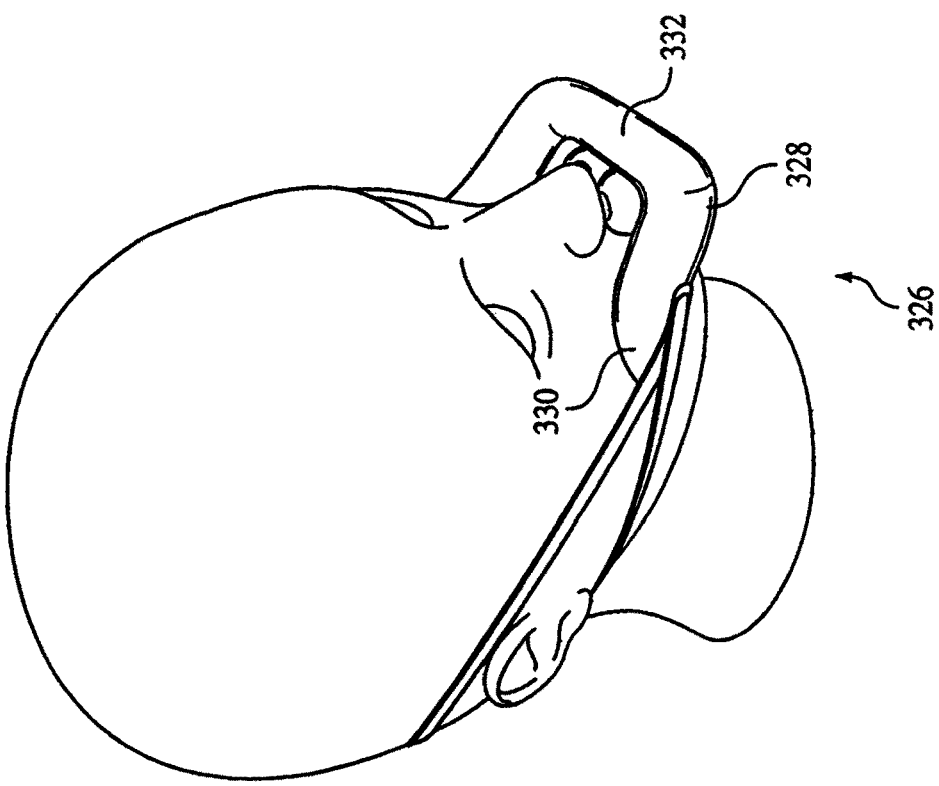

A seventh embodiment of a patient interface device 326 according to the principles of the present invention is shown in FIGS. 32A and 32B. The patient interface device in this embodiment is similar to that discussed above with respect to FIGS. 27A-31C except that in the present embodiment, patient interface device 326 does not include the patient contacting members. Instead, support member 328 includes patient contacting portions 330 that rest on the surface of the patient.

Support member 328 is generally U-shaped and the end of each leg of the "U" rests on the patient. Of course, padding is provided on the end of each leg for optimum patient comfort. In addition, patient contacting portions 330 have a patient contacting surface that is contoured to correspond to the features of a human face. Headgear straps 331 are also connected near the end of each leg of the U-shaped support member.

Support member 328 includes a sealing assembly coupling portion 332 to which a sealing assembly is attached. The sealing assembly that can be coupled to the support member is any of the sealing assemblies discussed herein, such as the nasal cannula or nasal pong types of seals. Although not shown in the illustrated embodiment, a patient circuit connects to support member 328 at any location on the support member, and a gas flow path is defined in the support member from the point where the patient circuit is connected to sealing assembly coupling portion 332. This gas flow path communicates the flow of gas provided by the pressure support system with an airway of a patient.

Figure 33B:
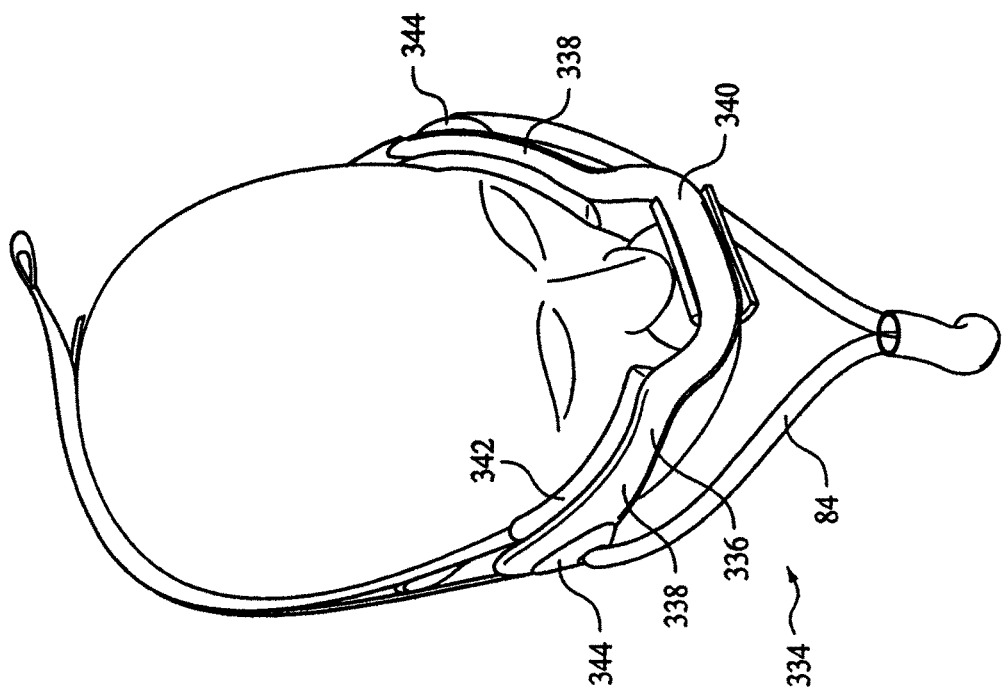
FIGS. 33A and 33B are perspective views of an eighth embodiment of a patient interface device according to the principles of the present invention shown on a patient.
Figure 33A:
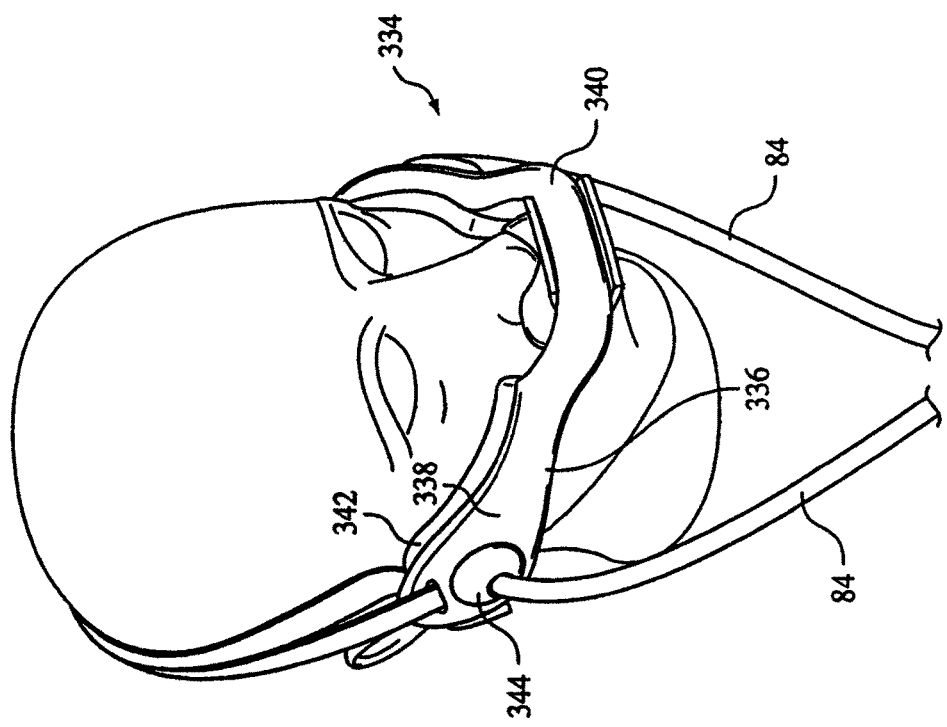

FIGS. 33A and 33B illustrate an eight embodiment of a patient interface device 334 according to the principles of the present invention. Patient interface device 334 is generally similar to that shown in FIGS. 32A and 32B except that a support member 336 includes a pair of relatively large cheek contacting portions 338 to maximize the disbursement of the strapping forces on the patient's face. The large cheek contacting portions also enhance the stability of the support member on the patient. Support member 336 includes a sealing assembly coupling portion 340 to which a sealing assembly is attached. The sealing assembly that can be coupled to the support member is any of the sealing assemblies discussed herein, such as the nasal cannula or nasal pong types of seals. A pad 342 is provided on the patient contacting side of the cheek contacting portions of the support member. In addition, cheek contacting portions 338 are contoured to correspond to the features of a human face. A rotateable coupling 344 is provided on each end of support member 336 so that conduits 84 are rotateably coupled to the support member.

Figure 34A:
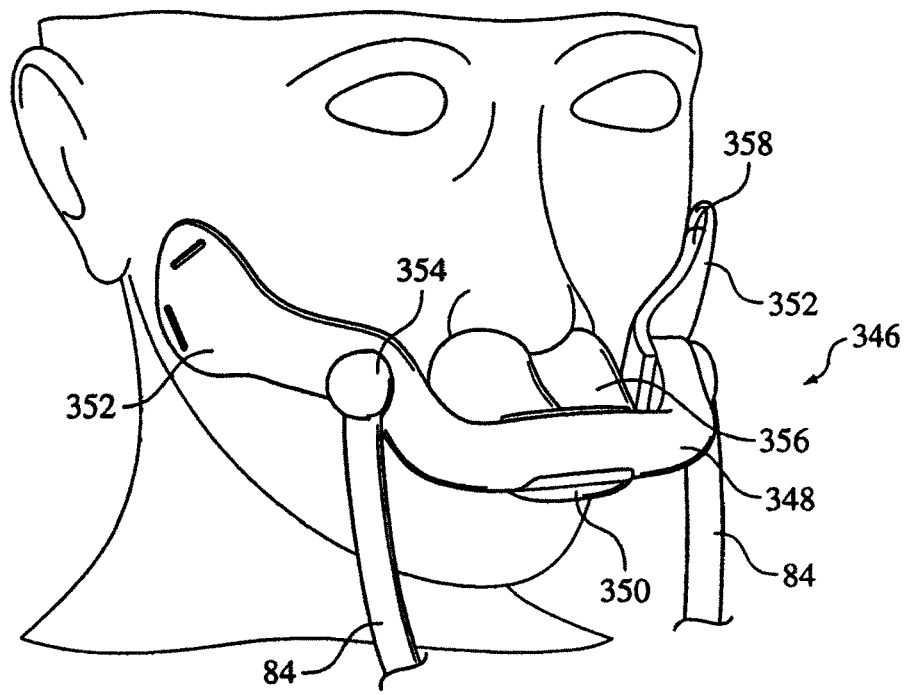
FIGS. 34A and 34B are perspective and side views, respectively, of a ninth embodiment of a patient interface device according to the principles of the present invention shown on a patient.
Figure 34B:
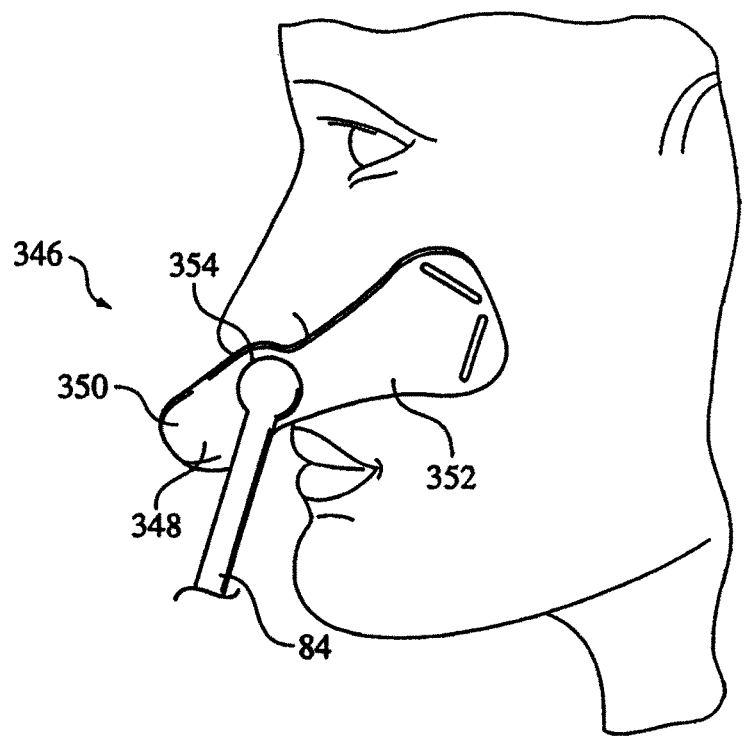

FIGS. 34A and 34B illustrate a ninth embodiment of a patient interface device 346 according to the principles of the present invention. Patient interface device 346 is generally similar to that shown in FIGS. 33A and 33B except that conduits 84 are coupled to a support member 348 at a location that is closer to a sealing assembly support portion 350 than in the earlier embodiment. Support member 348 still includes cheek contacting portions 352. However, the cheek contacting portions are provided at a posterior location relative to conduit couplings 354. Preferably, conduit coupling 354 rotateably couples conduits 84 to a hollow portion of support member 348 to communicate a flow of gas to a sealing assembly 356 mounted on sealing assembly support portion 350 of support member 348. This embodiment for patient interface device 346 reduces the amount of material provided on the face of the patient.

It should be noted that pads 358 are provided on the patient contacting sides of the cheek support portions of the support member. In addition, cheek contacting portions 352 have a patient contacting surface that is contoured to correspond to the features of a human face. Sealing assembly 356 is preferably rotateably coupled to support member 348 so that the patient can control the position of the sealing assembly relative to the support member. While nasal-cannula type of sealing assembly is shown, it is to be understood that any sealing assembly can be supported by the support member.

Figure 35B:
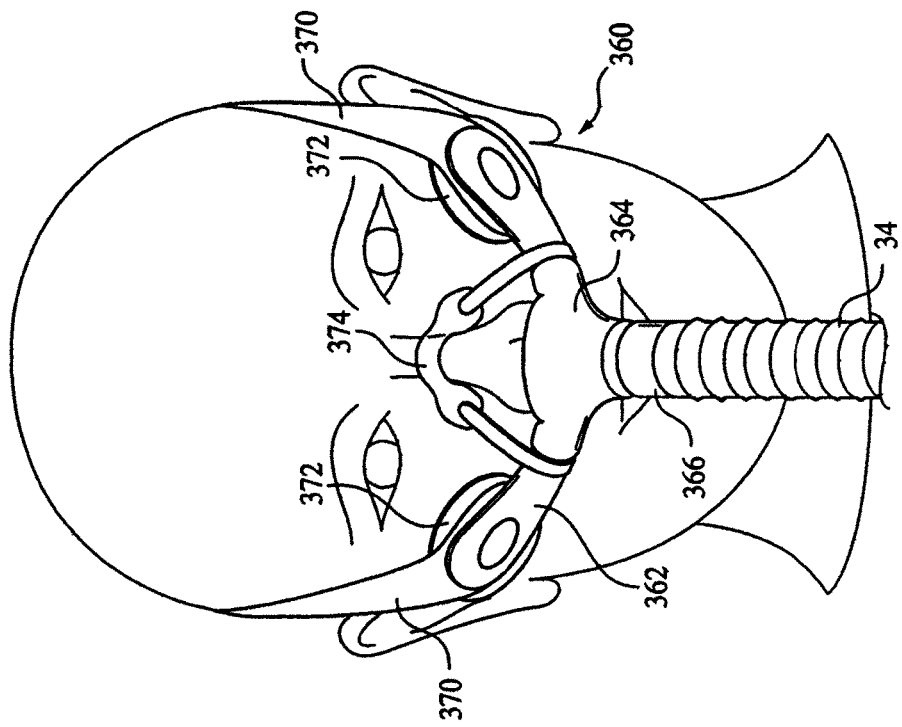
FIGS. 35A and 35B are perspective and front views, respectively, of a tenth embodiment of a patient interface device according to the principles of the present invention shown on a patient.
Figure 35A:
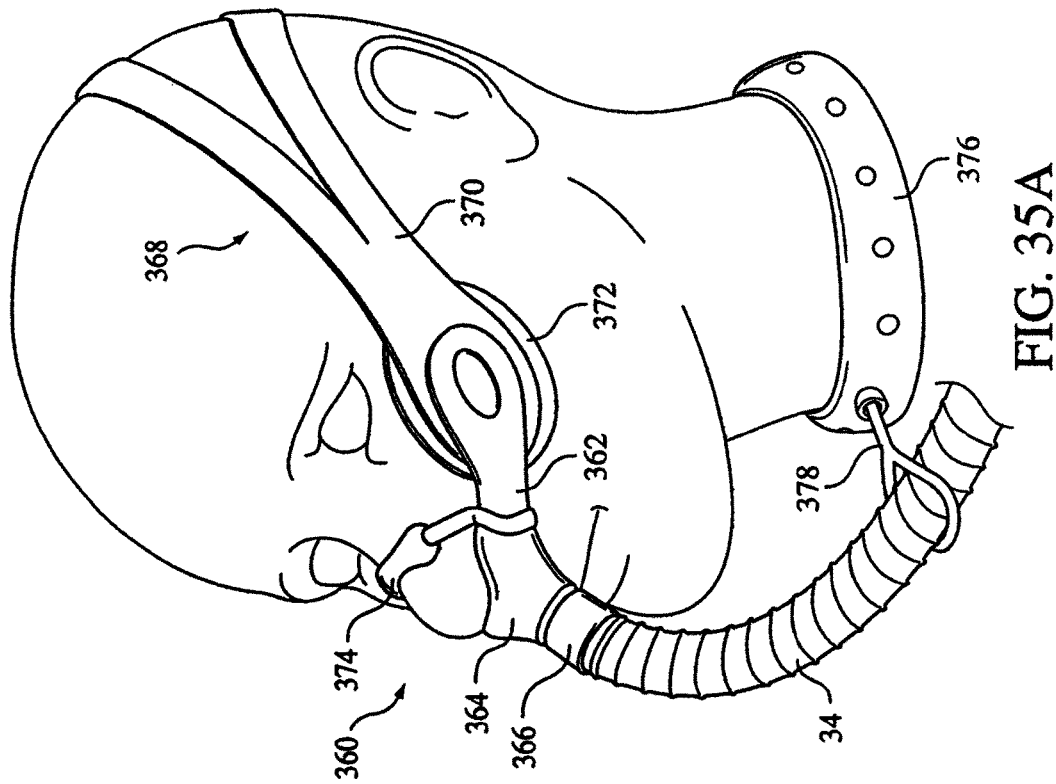

FIGS. 35A and 35B illustrate a tenth embodiment of a patient interface device 360 according to the principles of the present invention. Patient interface 360 is similar to that of FIGS. 27A-34, except that in this embodiment, patient circuit 34 is coupled to a central portion 364 of a support member 362 via a coupling 366. Coupling 366 is preferably a swivel coupling so that patient circuit 34 is rotateable relative to support member 362. Central portion 364 of support member 362 also serves as the sealing assembly, for example, by including prongs that extend from the patient side of the support member or by providing an opening on the patient contacting side of the support member. Of course, the support member should be formed from a material suitable to function as the sealing assembly. It is to be understood that a separate sealing assembly can be coupled to the support member, as in the previous embodiments instead of having the support member function as its own sealing assembly.

A headgear assembly 368 having a pair of headgear straps 370 is coupled to support member 362. A pad 372 is provided between the patient and the location where the headgear strap and the support member are joined. A nose piece 374 is also coupled to support member 362. In an exemplary embodiment of the present invention, nose piece 374 is a nasal dilating device that adheres to the lateral surfaces of each nostril and is biased so as to distend the nostrils outward. It is generally understood that deflecting the surface of the nostril outward, opens or widens the nasal passages to reduce the resistance of the flow of gas through the nasal passages.

Finally, a collar 376 connects the patient to patient circuit 34 via a coupling member 378. Attaching the patient circuit to the patient in this manner helps manage the patient circuit to keep it under control while the pressure support system is being used. Although collar 376 is shown attached to the patient's neck, it is to be understood that the collar can be attached to other locations of the patient, such as the shoulder, thorax, arm, and/or waist.

Figure 36A:
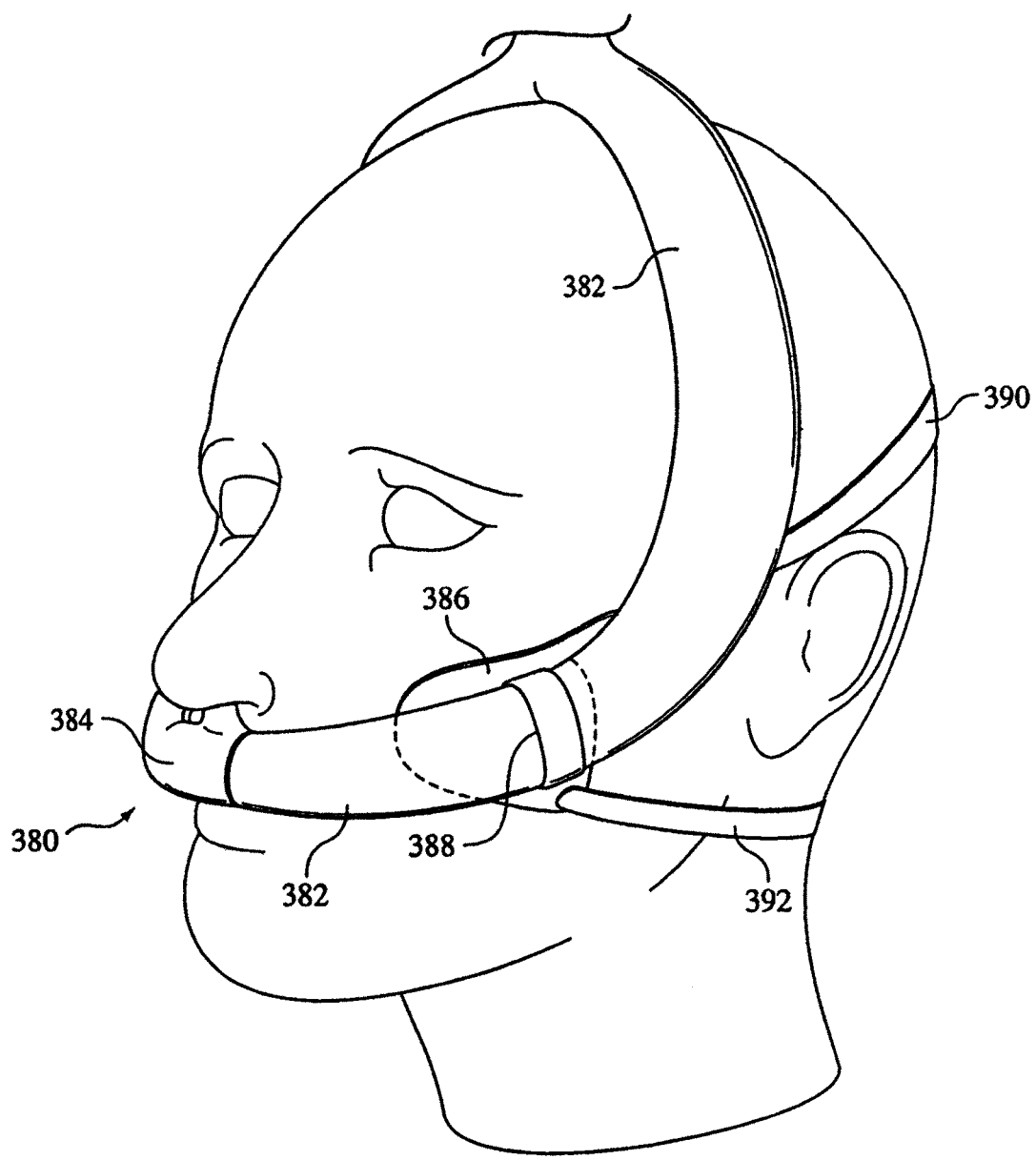
FIG. 36A-36C are perspective, front, and side views, respectively, of an eleventh embodiment of a patient interface device according to the principles of the present invention shown on a patient.
Figure 36C:
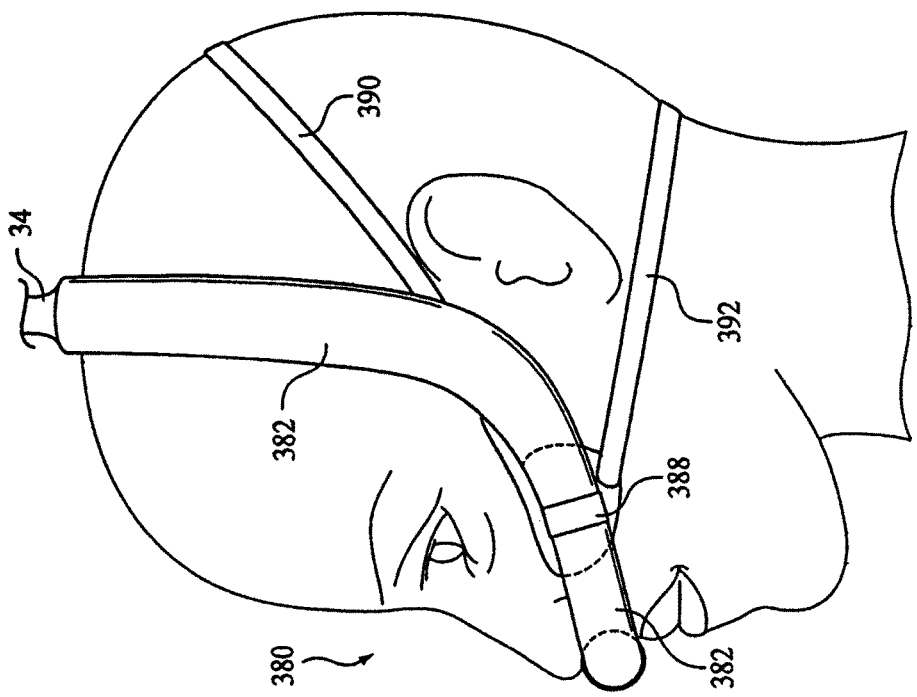
Figure 36B:
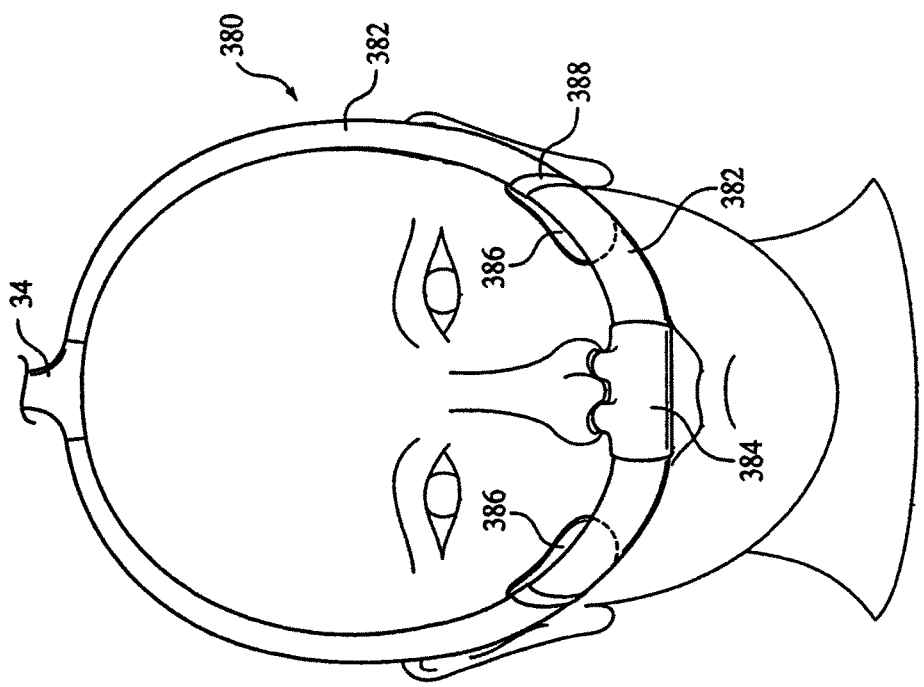

FIG. 36A-36C illustrate an eleventh embodiment of a patient interface device 380 according to the principles of the present invention. Patient interface device 380 includes a support member 382 that is coupled to a sealing assembly support 384. A unique feature of support member 382 is that it extends from under the patient's nose, across the cheeks, up the sides of the head, and over the top of the patient's head, where it joins with patient circuit 34. Preferably, support member 382 is formed from a crush resistant tubing, so that the patient can lie on his or her side while using the pressure support system coupled to patient interface device 380 without impairing the flow of gas to the patient.

In an exemplary embodiment of the present invention, sealing assembly support 384 itself serves as the sealing assembly, for example, by including prongs or a patient contacting cushion integral with the sealing assembly support. Alternatively, a separate sealing assembly having any of the configurations discussed above can be attached to the sealing assembly support. Sealing assembly support 384 is either integral with support member 328 or is coupled thereto, so that the sealing assembly or the sealing assembly support member can be selectively attached to the support member. If the sealing assembly support is not integral with the support member, it is preferable that the sealing assembly support is rotateable relative to the support member.

A patient contacting member 386 is coupled to support member 382. Patient contacting member 386 is a single or multiple-piece assembly that includes a headgear attachment portion and a patient contacting portion. The patient contacting portion of patient contacting member 386 is preferably contoured to correspond to the facial features of the patient, and is preferably easily removable from the support member so that the patient contacting portion can be easily replaced. In the illustrated embodiment, a loop 388 connects patient contacting member 386 to support member 382. A pair of headgear straps 390 and 392 are connected to patient contacting member 386 to assist in securing patient interface device 380 to the face of the patient.

Figure 37:
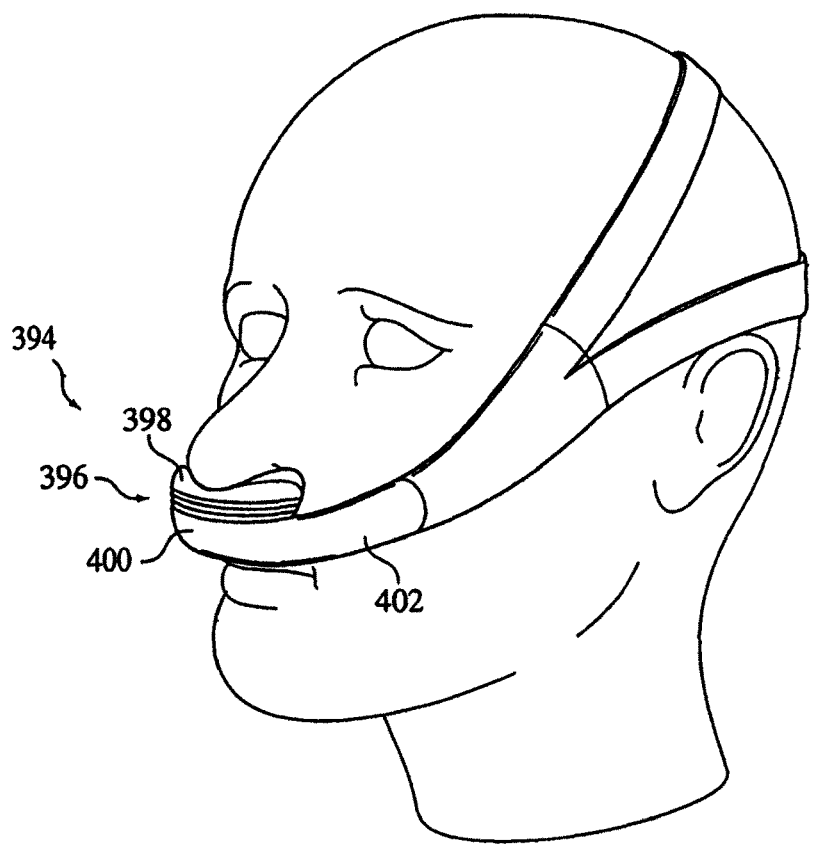
FIG. 37 is a perspective view of a twelfth embodiment of a patient interface device according to the principles of the present invention shown on a patient.
Figure 38:
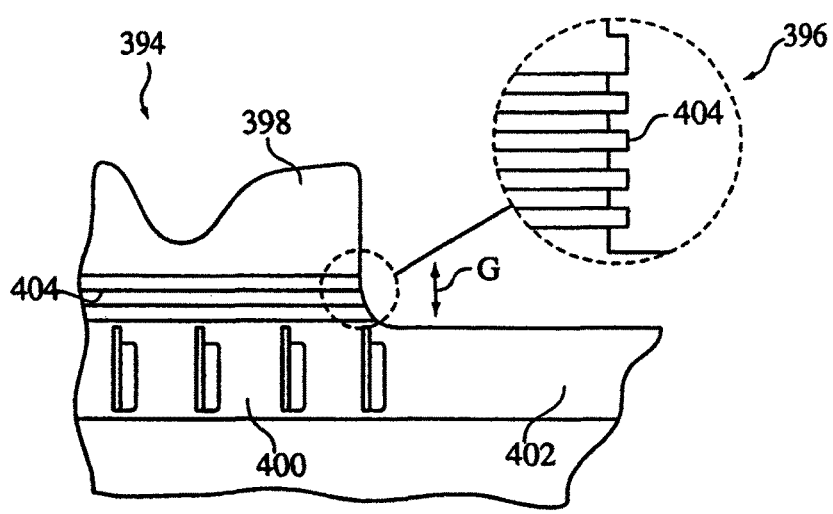
FIG. 38 is a side and detailed view of a portion of the patient interface device of FIG. 37.

FIGS. 37 and 38 illustrate a twelfth embodiment of a patient interface device 394 according to the principles of the present invention. Patient interface device 394 includes the features of the present invention discussed above, in addition to a sealing assembly extending portion 396. Sealing assembly extending portion 396 moves a sealing assembly 398 in a direction, as indicated by arrow G, toward and away from a sealing assembly support portion 400 of a support member 402.

In an illustrated exemplary embodiment of the present invention, sealing assembly extending portion 396 is formed from a corrugated segment 404 that can be extended or retracted as desired to position sealing assembly 398 at the airway of the patient. Preferably, corrugated segment 404 permits movement of sealing assembly 398 to the desired position, yet is resistant to inadvertent movement so the sealing assembly is not easily dislodged from the airway of the patient.

Figure 39:
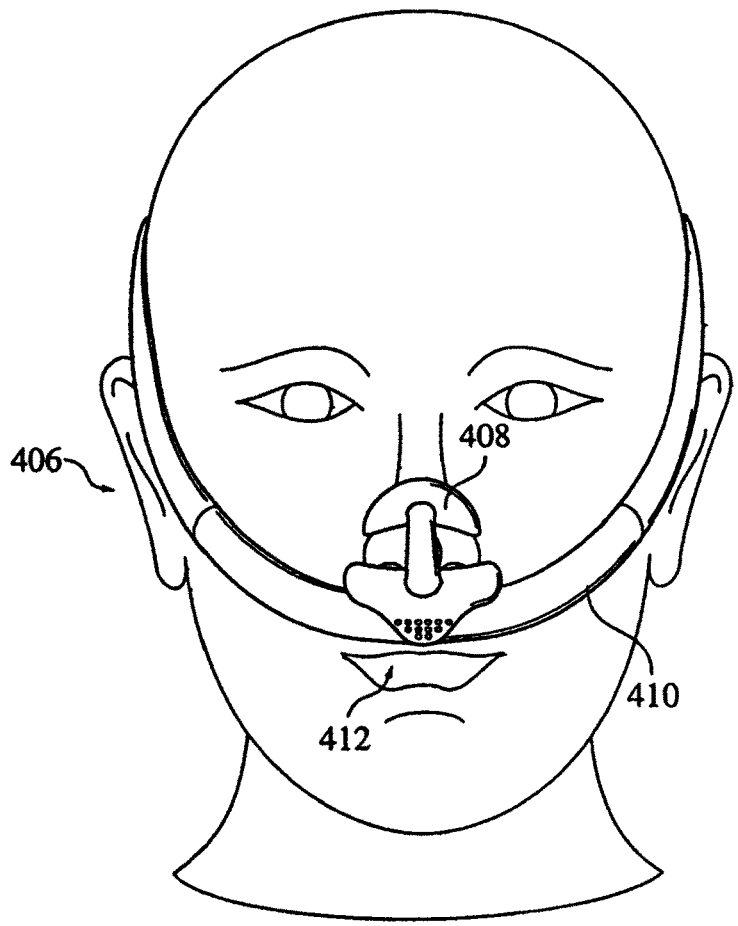
FIG. 39 is a front view of a thirteenth embodiment of a patient interface device according to the principles of the present invention shown on a patient.

FIG. 39 illustrates a thirteenth embodiment of a patient interface device 406 according to the principles of the present invention. Patient interface device 406 is similar to the patient interface devices discussed above, except that a nose contacting portion 408 is provided to facilitate attachment of a support member 410 to a face of a patient. Nose contacting portion 408 extends from support member 410 over the tip of the nose and contacts the nose above the tip. The present invention contemplates that nose contacting portion 408 can be adhered to the nose or simply rest on the nose without being adhered thereto. This embodiment also illustrates an exhaust assembly 412 in the form of a plurality of vent ports provided at the central portion of support member 410.

Figure 40:
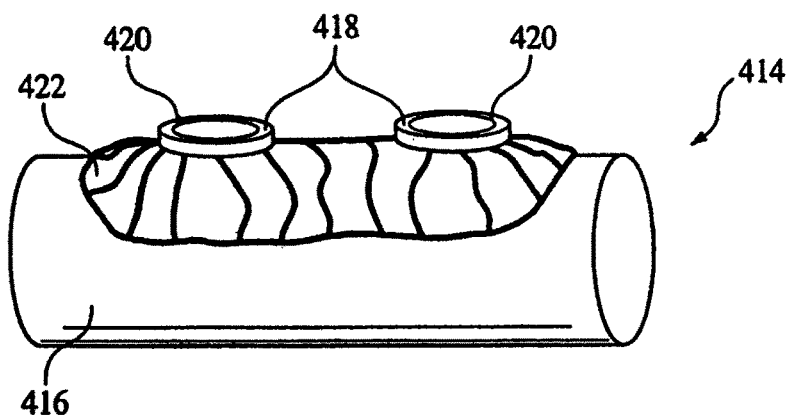
FIG. 40 is a perspective view of a further embodiment for a sealing assembly suitable for use with the patient interface device of the present invention.

FIG. 40 is a perspective view of a further embodiment for a sealing assembly 414 suitable for use with the patient interface devices of the present invention. Sealing assembly 414 includes a base portion 416 and a pair of prongs 418 coupled thereto. The base portion couples with the support member in any of the embodiments for the patient interface device discussed herein. Each prong includes a passage 420 that communicates an airway of a patient with an interior of the base portion.

A unique feature of sealing assembly 414 is that it includes a sealing material 422 disposed around each prong. In an exemplary embodiment of the present invention, sealing material 422 is a conformable substance that the user shapes or molds to provide a customized seal for each prong. Once molded to the desired shape, sealing material 422 preferably retains that shape. Therefore, this embodiment of the present invention contemplates that sealing material 422 must be activated, for example by heating, in order for the shape of that material to be changed.

In another embodiment, which can be used alone or in combination with the customizable feature of the first embodiment, sealing material 422 includes an adhesive property to assist in maintaining a good seal with the patient when the patient interface device is worn by the patient. Thus, sealing material 422 can be a somewhat sticky puddy that is moldable to the features of the user and provides a good seal with the user's skin.

Figure 41:
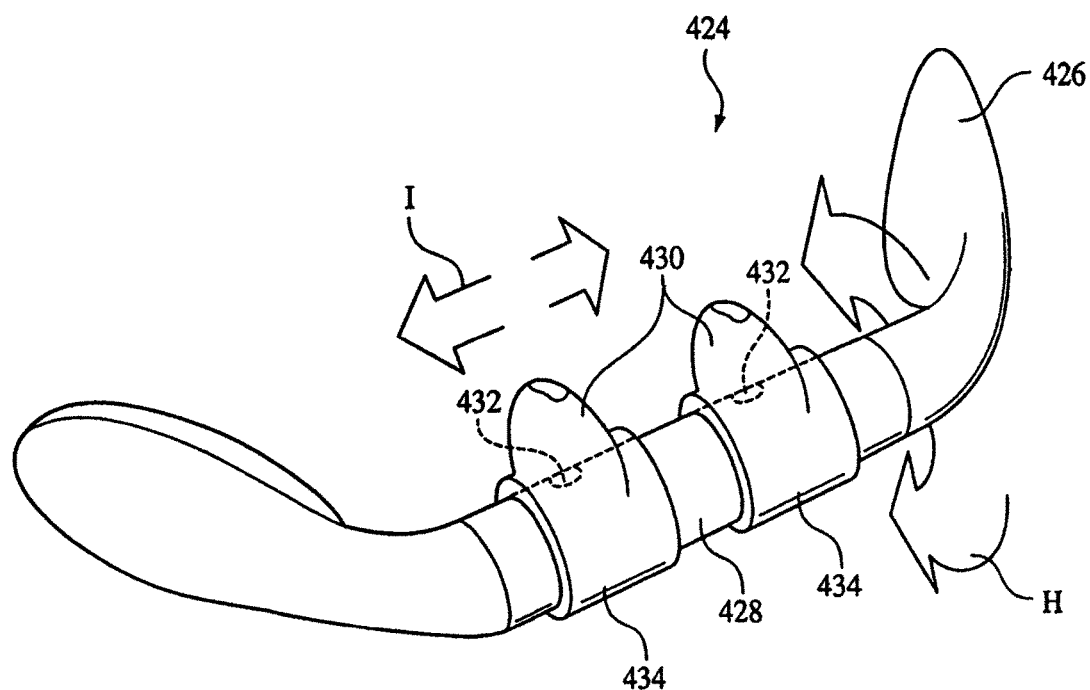
FIG. 41 is a perspective view of a fourteenth embodiment of a patient interface device according to the principles of the present invention shown on a patient.
Figure 42:
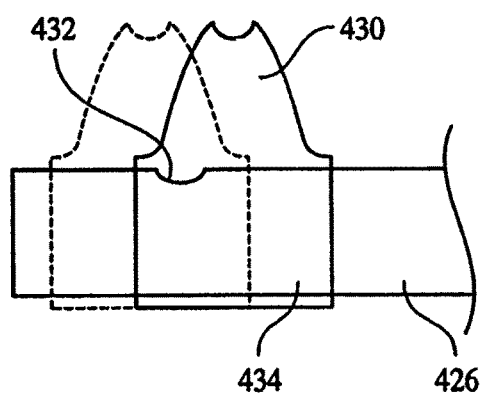
FIG. 42 is a side view of a portion of the patient interface device of FIG. 41 showing the movement of the nasal prongs on the support member.

A fourteenth embodiment of a patient interface device 424 according to the principles of the present invention is shown in FIGS. 41 and 42. Patient interface device 424 includes a support member 426 that is coupled to a flow of gas (not shown) using any coupling technique. A gas flow path is defined in the support member from the point where the patient circuit is coupled to the support member to a sealing assembly support 428 on which are located a pair of nasal prongs 430. Openings 432 are defined in the sealing assembly support to communicate a flow of gas to an interior of each prong.

In an exemplary embodiment of the present invention, sealing assembly support 428 is rotateably coupled to support member 426 so that the rotational angle of the nasal prongs relative to the support member can be changed, as indicated by two-headed arrow H. The coupling of the support member with the sealing assembly support can be a ratchet-type of coupling that allows the sealing assembly support to be located in discrete positions relative to the support member. Alternatively, the coupling between the support member and the sealing assembly support can provide a continuous range of adjustability.

Nasal prongs 430 are coupled to support member 426 such that the nasal prongs can slide, either independently or together, along a longitudinal axis of the support member, as indicated by two-headed arrow I in FIG. 41. The sliding displacement of one of the prongs is shown in FIG. 42. Nasal prongs 430 can be coupled to support member 426 in a variety of ways that provide this sliding capability. An example of one such technique for slideably securing the nasal prongs to the support member is shown in FIGS. 41 and 42. In this illustrated embodiment, each prong is attached to or integral with a coupling sleeve 434. The coupling sleeve is provided around the support member such that the sleeve slides along the length of the support member while still providing a good seal with the support member, so that gas provided through opening 432 does not leak around the sleeve. It can be appreciated that the nasal prongs can move along the length of the support member in the same direction or in opposite directions to alter the distance between the prongs. The amount of movement along the support member is not limited, so long as an interior of the prongs remains in fluid communication with opening 432 so that the flow of gas is communicated to the prong.

Figure 43:
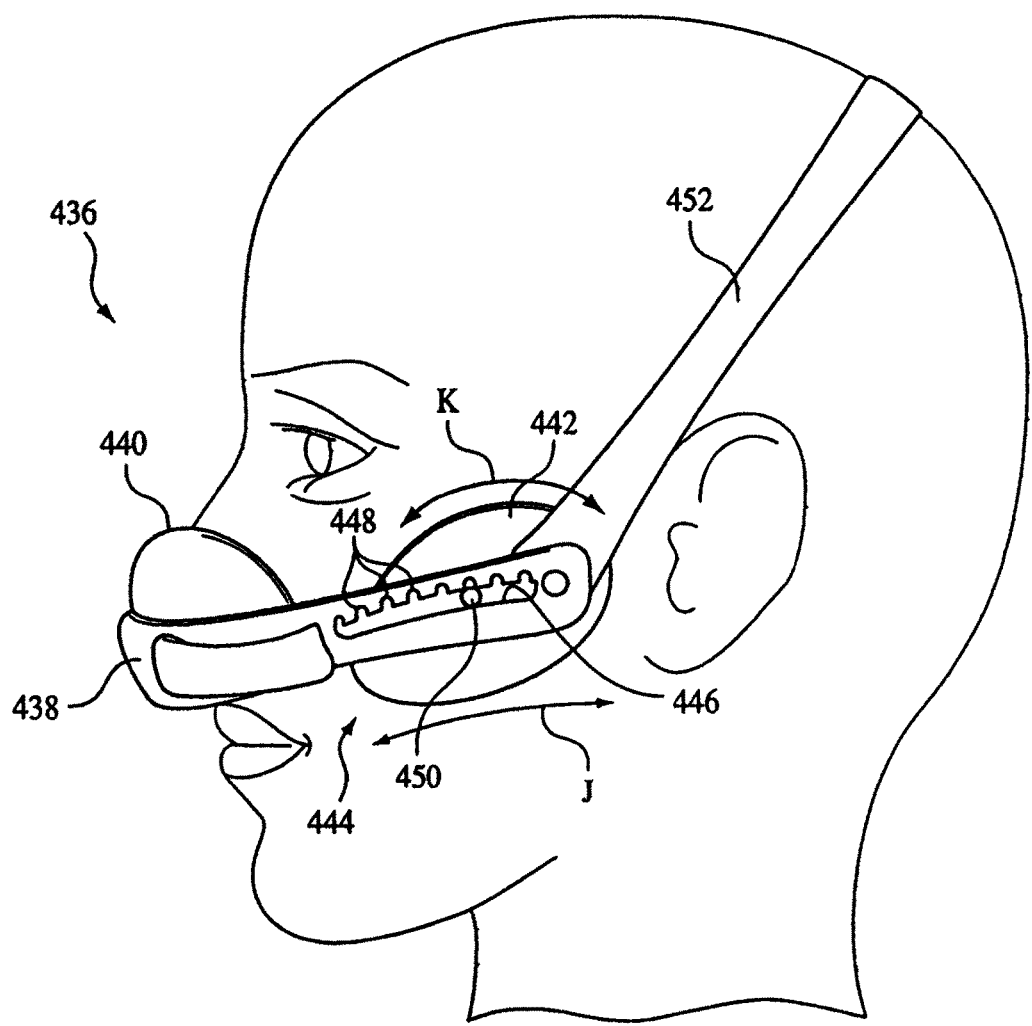
FIG. 43 is a side view of a fifteenth embodiment of a patient interface device according to the principles of the present invention shown on a patient.

FIG. 43 illustrates a fifteenth embodiment of a patient interface device 436 according to the principles of the present invention. Patient interface device 436 includes a support member 438 that supports a sealing assembly 440. Support member 438 is either hollow or partially hollow to communicate a flow of gas from a patient circuit (not shown) to the sealing assembly or the flow of gas is coupled directly to the support assembly. A patient contacting member 442 is coupled to the support member. In this embodiment, the position of the patient contacting member along the length of the support member is adjustable, as indicated by arrow J, by means of an adjustment assembly, generally indicated at 444, that connects the patient contacting member and the support member.

In the illustrated exemplary embodiment, adjustment assembly 444 includes a track 446 with a plurality of notches 448 disposed on support member 438. Patient contacting member 442 includes a pin 450 disposed in track 446. When pin 450 is located in one of the notches, patient contacting member 442 can rotate or swivel about the pin, as indicated by arrow K. Pin 450 can be moved along the length of the support member to other notches, thereby changing the position of the patient contacting member on the support member. The notches provide discrete locations in which the pin can be located and held. A headgear strap 452 is connected to support member 438, as shown, or is connected to the patient contacting member in any fashion, including the headgear attachment techniques discussed above.

Figure 44:
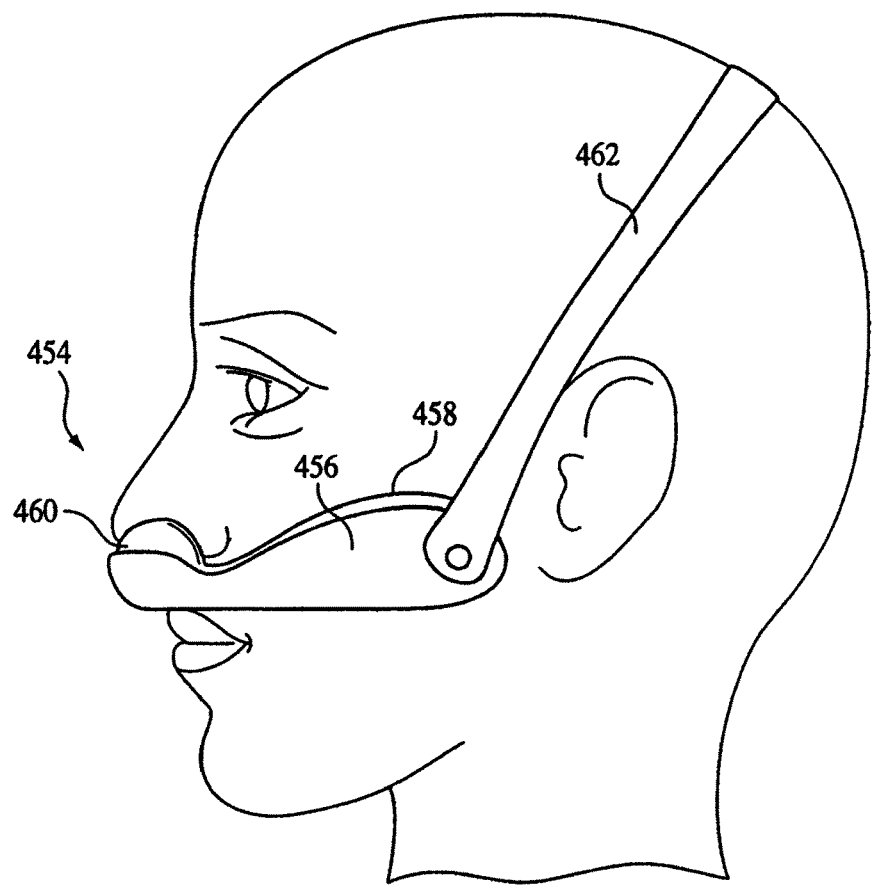
FIG. 44 is a side view of a sixteenth embodiment of a patient interface device according to the principles of the present invention shown on a patient.
Figure 45:
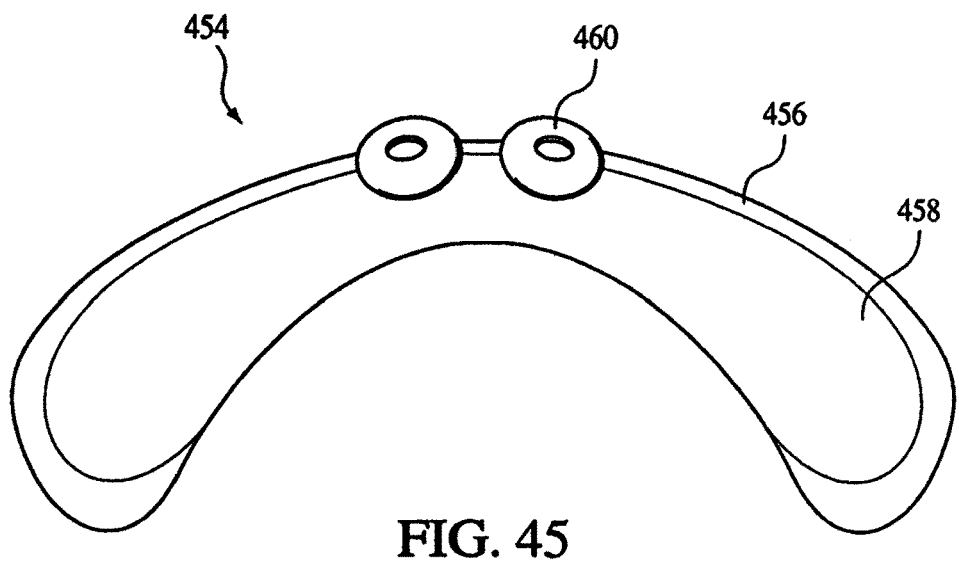
FIG. 45 is a rear view of the patient interface device of FIG. 44.

FIGS. 44-45 illustrate a sixteenth embodiment of a patient interface device 454 according to the principles of the present invention. Patient interface device 454 includes a support member 456 that spans the face of the user. An inflatable bladder 458 is coupled to the patient side of the support member. In the illustrated exemplary embedment, inflatable bladder is sized and shaped so as to generally match a major portion of the support member. The bladder can be filed at all times or can be filled by the flow of gas delivered through the patient circuit (not shown). In the latter configuration, a sealing assembly 460 is coupled directly to the bladder such that gas from the bladder passes to the airway of the patient through the sealing assembly. In the illustrated embodiment, sealing assembly 460 is a pair of nasal prongs. It is to be understood that other types of sealing assemblies, such as a cushion, can be used.

Bladder 458 can rest directly on the surface of the patient or a padding can be provided between the bladder and the patient. A headgear strap 462 is connected to support member 456 in any fashion, including the headgear attachment techniques discussed above.

FIGS. 46-49 illustrate an alternative configuration or technique for attaching a sealing assembly 502 to a support member 504 in a patient interface device 500. In this embodiment, a snap assembly, generally indicated at 506, is provided to selective couple the sealing assembly to the support member. More specifically, the snap assembly includes at least one tab 508 associated with the sealing assembly and corresponding grooves 510 associated with the support member. In the illustrated embodiment, three tabs and grooves are provided on the sealing assembly and support member.

It is to be understood that the number of tabs and groove, their location, and their configuration can be altered while remaining within the spirit of the present invention. For example, the present invention contemplates providing the tabs on support member 504 and the grooves on the sealing assembly 502. It should also be understood that the sealing assembly and the support member can also have configurations other than those illustrated in FIGS. 46-49. For example, the sealing assembly can include nasal prongs as described above.

In the illustrated exemplary embodiment, tabs 508 are defined by a support frame 512 that forms part of the sealing assembly. More specifically, the sealing assembly is defined by a patient contacting member 511, such as the cushion or nasal prongs, and the support frame. In an exemplary embodiment, support frame 512 is formed from a relatively rigid material so that it provides strong and secure points of attachment for the sealing assembly to the support member. In an exemplary embodiment, support frame 512 is formed from a rigid plastic or metal. Of course, the present invention also contemplates forming the support frame or portions thereof from other materials, including semi-rigid or flexible materials.

The support frame and the patient contacting member can be coupled to one another in any conventional manner. However, in an exemplary embodiment, the patient contacting member is molded over the support frame. To ensure a secure attachment of the patient contacting member to the support frame, a plurality of openings 514 are formed in the support frame so that the material defining the patient contacting member can flow into these openings. The patient contacting member is molded to the support frame such that tabs 508 protrude from the surface of the patient contacting member to engage the grooves in the support member.

Figure 46:
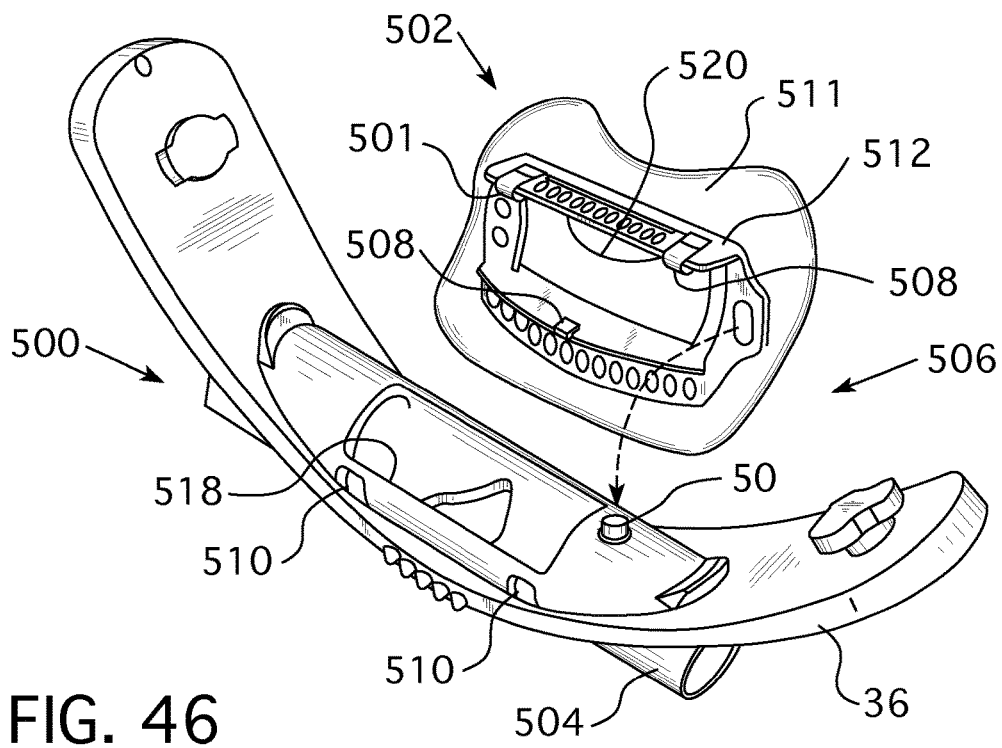
FIG. 46 is a perspective view showing an alternative configuration for attaching a sealing assembly to a support member.
Figure 47:
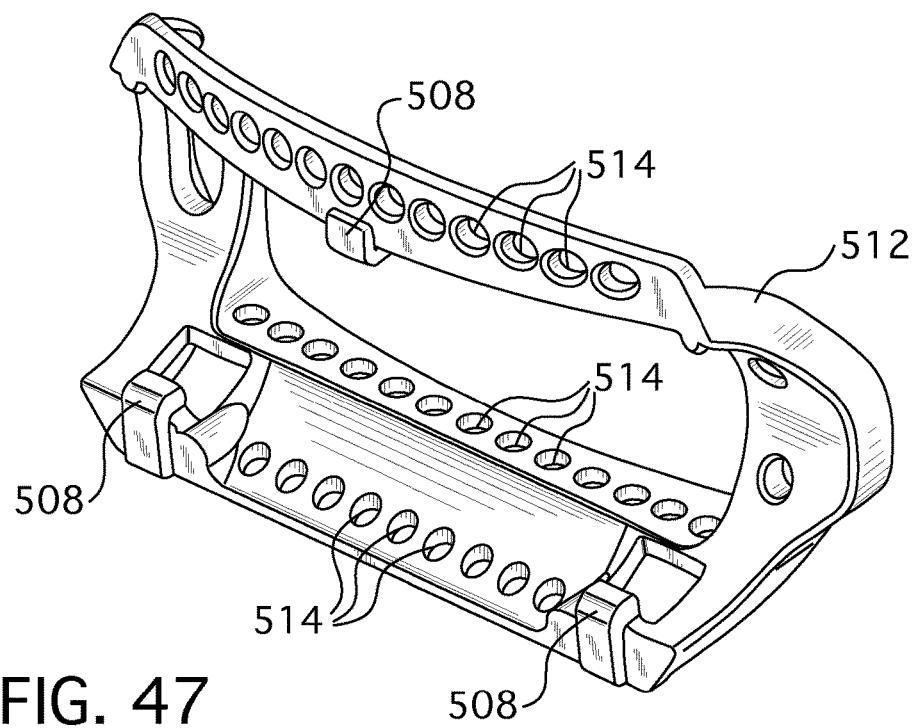
FIG. 47 is a perspective view of a support frame used in the sealing assembly of FIG. 46.
Figure 48:
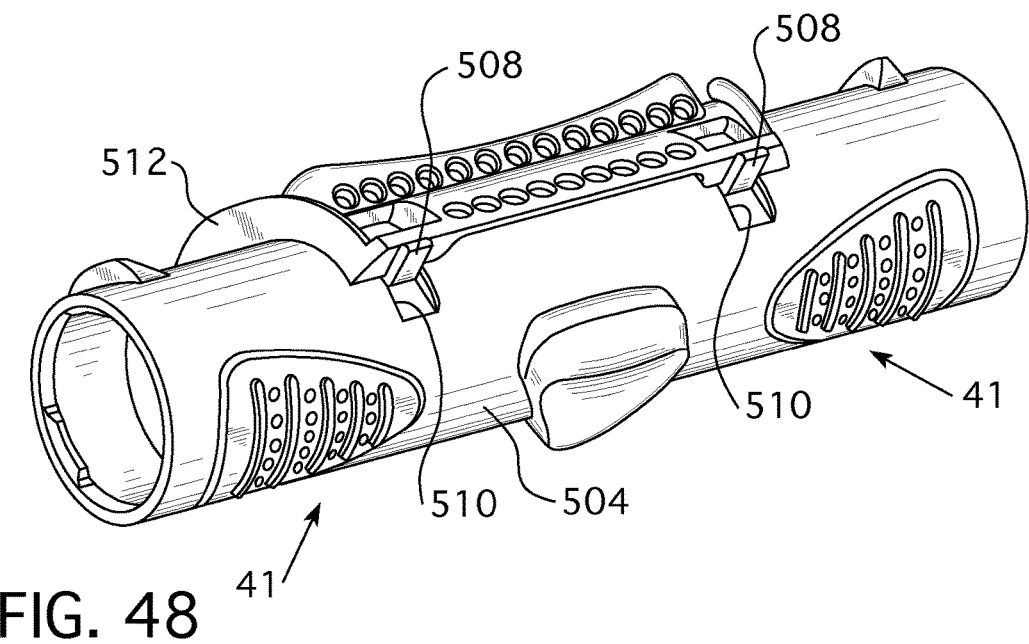
FIG. 48 is a perspective view illustrating the attachment of the support frame to the support member in the embodiment of FIG. 46.
Figure 49:
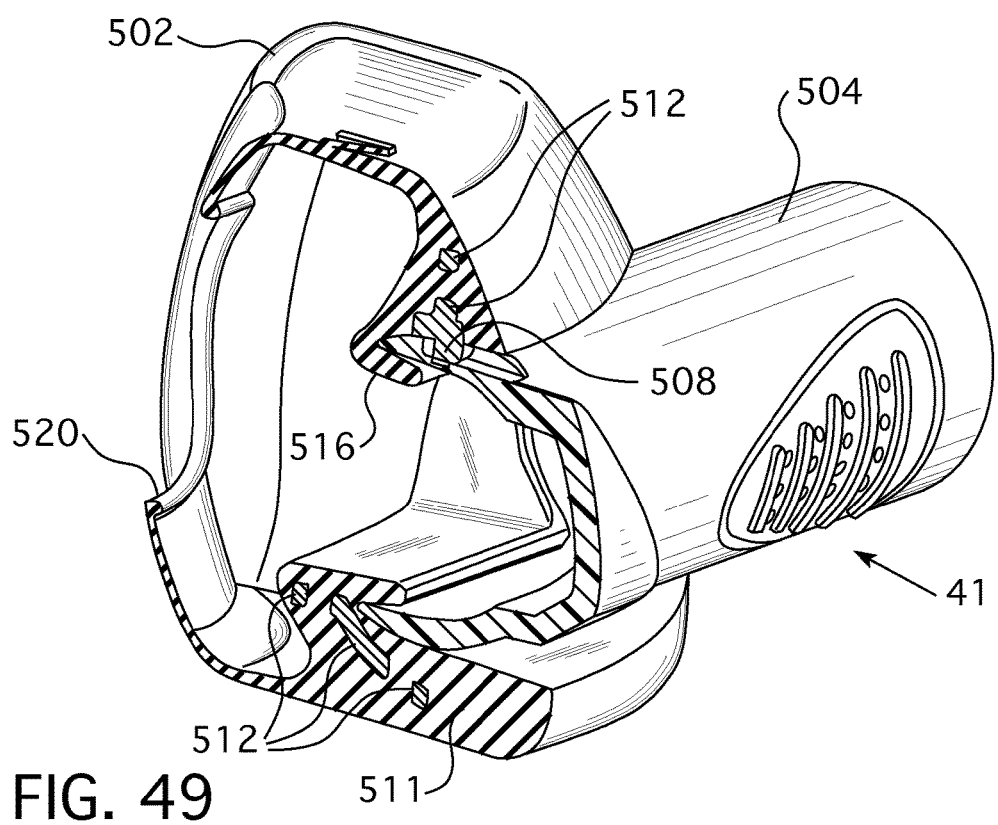
FIG. 49 is a cross sectional view of the attachment of the sealing assembly to the support member in the embodiment of FIG. 46.

As perhaps best shown in FIGS. 46 and 49, sealing assembly 502 includes a first opening 516 that corresponds or mates with a corresponding opening 518 in support member 504. Sealing assembly 502 also includes a second opening 520 to communicate an interior of the seal with an airway of the patient.

By allowing the sealing assembly to snap onto the support member in a secure and stable fashion while still allowing the sealing assembly to be removed from the support member, it becomes very easy to remove the sealing assembly for cleaning purposes and reattach it. This also allows for a great degree of flexibility in the size, configuration, shape, material, etc, for the sealing member, in that any such sealing member can be used in conjunction with the support member. The support frame also serves to provide a stable and secure attachment of the sealing member to the support member.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a support member sized and configured to span at least a portion of a patient's face while remaining below the patient's eyes responsive to the patient interface device being donned by such a patient, the support member being a single-piece unitary member and having a coupling portion configured to continuously span from a first side of a patient's face on a first side of the patient's nose to a second, opposite side of the patient's face on a second, opposite side of the patient's nose responsive to the patient interface device being donned by such a patient;
   a sealing assembly operatively coupled to the support member at the coupling portion in a manner wherein the sealing assembly is rotatable relative to the support member about a longitudinal axis of the coupling portion and slideable relative to the support member along the longitudinal axis of the coupling portion while remaining in fluid communication with an interior of the support member, wherein the support member defines a gas carrying conduit adapted to carry a flow of gas to the sealing assembly; and
   a pair of patient contacting members, each contacting member adjustably coupled to the support member at a location on the support member positioned to overlie a respective zygomatic bone of the patient when the patient interface device is donned by the patient,
   wherein each contacting member of the pair of contacting members comprises a pad support adjustably coupled to the support member and a pad attached to the pad support opposite the support member, and
   wherein the pad is structured to engage the respective zygomatic bone of the patient when the patient interface device is donned by the patient.

2. The interface device of claim 1, wherein the sealing assembly includes a pair of nasal prongs, wherein each prong is structured to insert at least partially into a nostril of such a patient.

3. The interface device of claim 1, wherein the pair of patient contacting members include a headgear attachment portion.

4. The interface device of claim 3, further comprising a headgear assembly operatively coupled to the headgear attachment portion.

5. The interface device of claim 4, wherein the headgear assembly is rotateably attached to the headgear attachment portion.

6. The interface device of claim 1, further comprising an exhaust assembly disposed on the support member.

7. The interface device of claim 1, wherein the support member is adapted to span a patient's face such that the longitudinal axis is generally parallel to an axis defined through such a patient's eyes.

8. The interface device of claim 1, wherein the pad of each contacting member is detachably attached to the corresponding pad support.

9. The interface device of claim 1, wherein the pad of each contacting member is permanently attached to the corresponding pad support.

* * * * *